United States Patent
Steinmetz

(10) Patent No.: US 12,203,073 B2
(45) Date of Patent: *Jan. 21, 2025

(54) PLANT VIRAL RNA DELIVERY NANOPARTICLES AND USES THEREOF

(71) Applicant: CASE WESTERN RESERVE UNIVERSITY, Cleveland, OH (US)

(72) Inventor: Nicole F. Steinmetz, San Diego, CA (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 393 days.

This patent is subject to a terminal disclaimer.

(21) Appl. No.: 17/129,463

(22) Filed: Dec. 21, 2020

(65) Prior Publication Data

US 2021/0189396 A1 Jun. 24, 2021

Related U.S. Application Data

(60) Provisional application No. 62/951,143, filed on Dec. 20, 2019.

(51) Int. Cl.
| | | |
|---|---|---|
| C07H 21/04 | (2006.01) | |
| A61K 45/06 | (2006.01) | |
| A61K 47/62 | (2017.01) | |
| A61K 47/69 | (2017.01) | |
| C12N 7/00 | (2006.01) | |
| C12N 15/113 | (2010.01) | |

(52) U.S. Cl.
CPC .......... *C12N 15/1135* (2013.01); *A61K 45/06* (2013.01); *A61K 47/62* (2017.08); *A61K 47/6929* (2017.08); *C12N 7/00* (2013.01); *C12N 2310/14* (2013.01); *C12N 2770/14023* (2013.01)

(58) Field of Classification Search
None
See application file for complete search history.

(56) References Cited

U.S. PATENT DOCUMENTS

| | | |
|---|---|---|
| 5,004,606 A | 4/1991 | Frincke |
| 9,925,281 B2 | 3/2018 | Steinmetz et al. |
| 10,086,095 B2 | 10/2018 | Steinmetz et al. |
| 10,207,014 B2 | 2/2019 | Steinmetz et al. |
| 10,478,510 B2 | 11/2019 | Steinmetz |
| 11,020,497 B2 | 6/2021 | Steinmetz et al. |
| 11,167,047 B2 | 11/2021 | Steinmetz et al. |
| 11,253,610 B2 | 2/2022 | Steinmetz |
| 2005/0019270 A1 | 1/2005 | Finlay et al. |
| 2007/0248617 A1 | 10/2007 | Bachmann et al. |
| 2007/0258889 A1 | 11/2007 | Douglas et al. |
| 2007/0284545 A1 | 12/2007 | Isacsson et al. |
| 2010/0183504 A1 | 7/2010 | Chen |
| 2015/0033418 A1 | 1/2015 | Lommel et al. |
| 2015/0265696 A1 | 9/2015 | Gourapura et al. |
| 2020/0179468 A1 | 6/2020 | Steinmetz |
| 2022/0211881 A1 | 7/2022 | Steinmetz |

FOREIGN PATENT DOCUMENTS

| | | |
|---|---|---|
| JP | 2009524699 A | 7/2009 |
| WO | 200118199 A1 | 3/2001 |
| WO | 2001/0026682 A2 | 4/2001 |
| WO | 2003092623 A2 | 11/2003 |
| WO | 2012078069 A1 | 6/2012 |
| WO | 2013181557 A1 | 12/2013 |
| WO | 2014059021 A1 | 4/2014 |
| WO | 2015/0039255 A1 | 3/2015 |
| WO | 2015/188110 A1 | 12/2015 |
| WO | 2016019393 A1 | 2/2016 |
| WO | 2016073972 A1 | 5/2016 |
| WO | 2016/149264 A1 | 9/2016 |
| WO | 2017/004123 A1 | 1/2017 |

OTHER PUBLICATIONS

Yildiz et al. (Applications of viral nanoparticles in medicine, Current Opinion in Biotechnology, vol. 22, Issue 6, 2011, pp. 901-908).*
Pretto et al. ("Versatile reversible cross-linking strategy to stabilize CCMV virus like particles for efficient siRNA delivery." Bioconjugate chemistry 30.12 (2019): 3069-3077).*
Mosquera et al. (Acc. Chem. Res. 2018, 51, 9, 2305-2313 Publication Date: Aug. 29, 2018.*
Imamura et al. ("FOXA1 promotes tumor progression in prostate cancer via the insulin-like growth factor binding protein 3 pathway." (2012)).*
Lam et al. (WIREs Nanomed Nanobiotechnol Jan./Feb. 2018 vol. 10: 1-18).*
Chiper, Manuela, Karen Niederreither, and Guy Zuber. "Transduction methods for cytosolic delivery of proteins and bioconjugates into living cells." Advanced Healthcare Materials 7.6 (2018): 1701040.*
Entire Futaki, Shiroh. ("Design and Creation of Functional Membrane-Interacting Peptides." Journal of Synthetic Organic Chemistry, Japan 78.11 (2020): 1058-1065).*
Of Liu, Na, et al. "FOXA1 and FOXA2: the regulatory mechanisms and therapeutic implications in cancer." Cell Death Discovery 10.1 (2024): 172).*
Applicant: Case Western Reserve University; "Cancer Immunotherapy Using Virus Particles"; European Patent Application No. 18764856.3 for Supplementary European Search Report dated Dec. 22, 2020; 8 pgs.
Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.
Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.
Nicole F.Steinmetz; "Viral Nanoparticle Multimers"; U.S. Appl. No. 14/761,444, filed Jul. 16, 2015; Final Office Action dated Mar. 11, 2021; 11 pgs.

(Continued)

Primary Examiner — Kimberly Chong
(74) Attorney, Agent, or Firm — Tarolli, Sundheim, Covell & Tummino LLP

(57) ABSTRACT

A nanoparticle includes an icosahedral-shaped plant virus particle; an RNAi construct; and one or more endolysosomal release agents, wherein the RNAi construct is noncovalently loaded within the icosahedral-shaped plant virus particle.

11 Claims, 6 Drawing Sheets

Specification includes a Sequence Listing.

(56) References Cited

OTHER PUBLICATIONS

"CWRU researcher to turn plant virus shells against human cancers", The Daily, CWRU Researcher to Turn Plant Virus Shells Against Human Cancers. Case Western Reserve University, Apr. 18, 2016.
Alaa A. Al. Aljabali, et al.; "CPMV-DOX Delivers", Molecular Pharmaceutics, vol. 10, No. 1, Jan. 7, 2013, pp. 3-10, XP055347068, US ISSN: 1543-8384, DOI: 10.1021/MP3002057.
Applicant: Case Western Reserve University; "Cancer Immunotherapy Using Virus Particles"; Canadian Office Action, dated Aug. 4, 2020; 3 pgs.
Applicant: Case Western Reserve University; "Plant Virus Particles for Delivery of Antimitotic Agents"; Extended European Search Report; dated Aug. 25, 2020; 11 pgs.
Canan Uluog, et al.: "Intermediate dose of methotrexate toxicity in non-Hodgkin lymphoma", General Pharmacology, vol. 32, 1999, pp. 215-218, XP55711259.
Chariou, et al., "Detection and Imaging of Aggressive Cancer Cells Using an Epidermal Growth Factor Receptor (EGFR)-Targeted Filamentous Plant Virus-Based Nanoparticle", Bioconjug Chem. Feb. 1, 20158; 26(2): 262-269.
European Search Report for Patent Application No. 15857504.3-1111/3215520, dated May 7, 2018.
Francisco, Joseph A., et al.; "CAC10-vcMMAE, an anti-CD30-monomethyl auristatin E conjugate with potent and selective anti-tumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.
International Search Report for Application No. PCT/US15/59675 (2016).
Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.
Jantipa Jobsri, et al.: Plant Virus Particles Carrying Tumour Antigen Activate TLR7 and Induce High Levels of Protective Antibody, Plos One, vol. 10, No. 2, Jan. 1, 2015, pp. 1-16, XP055347065, DOI: 10.1371/journal.pone.0118096.
Lee et al. "Biodegradable Viral Nanoparticle/Polymer Implants Prepared via Melt-Processing", ACS Nano ePub Sep. 13, 2017 vol. 11 No. 9 pp. 8777-8780.
Lee et al., "PEGylation to Improve Protein Stability During Melt Processing", Macromol Biosci 1-43, 57-75, Oct. 2015 vol. 15 No. 10 pp. 1332-1337.
Lizotte, et al., "Plant-derived viral-like nanoparticle immunotherapy suppress development of metastatic lung cancer", Journal of Immunology, vol. 194, Issue 1 Supplement, May 2015; 4 pgs.
Matsuura et al. Self-assembly of Ni-NT A-modified [3-annulus peptides into artificial viral capsids and encapsulation of His-tagged proteins. Org. Biomol. Chem., 2016, 14, 7869. DOI: 10.1039/c6ob01227b (Year: 2016).
Miermont et al., "Cowpea Mosaic Virus Capsid: A promising Carrier for the Development of Carbohydrate Based Antitumor Vaccines", Chem. Eur. J., 2008, vol. 14, pp. 4939-4947.
Nicole F. Steinmetz; U.S. Appl. No. 16/347,503, filed May 3, 2019; NonFinal Rejection dated Jun. 15, 2022; 36 pgs.
Nicole F. Steinmetz; U.S. Appl. No. 16/614,676, filed Nov. 18, 2019; NonFinal Rejection dated Jun. 3, 2022; 28 pgs.
Office action for Chinese Patent Application No. 201580063662.6, dated Mar. 4, 2020.
Office action for European Patent Application No. 15 857 504.3-1111, dated Mar. 18, 2020.
Office action for Japanese Patent Application No. 2017-524349, drafted Jan. 31, 2020; Mailed Feb. 10, 2020; 6 pgs.
Pfizer Ltd.: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].
Plchova et al. Expression of Human papillomavirus 16 E7ggg oncoprotein on N- and C-terminus of Potato virus X coat protein in bacterial and plant cells. Protein Expression and Purification 77 (2011); p. 146-152.
Sheen et al., "Stimulating Antitumor Immunity with Nanoparticles", Wiley Interdiscip Rev Nanomed Nanobiotechnol, Oct. 2014, vol. 6, pp. 496-505.
Smyth et al. Treatment of rapidly growing K-BALB and CT26 mouse tumours using Semliki Forest virus and its derived vector. Gene Therapy (2005) 12, 147-159.
Sourabh Shukla, et al.: "The Impact of Aspect Ratio on the Biodistribution and Tumor Homing of Rigid Soft-Matter Nanorods", Advanced Healthcare Materials, vol. 4, No. 6, Apr. 1, 2015, pp. 874-882, XP055473103, DE ISSN: 2192-2640, DOI: 10.1002/adhm.201400641.
Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, XP55711263.
Wen et al. Design of virus-based nanomaterials for medicine, biotechnology, and energy. Chem. Soc. Rev., 2016, 45, 4074. DOI: 10.1039/c5cs00287g (Year: 2016).
Chinese Patent Appl. No. 201580063662.6; Chinese Office Action; May 5, 2022; 3 pgs.
Agrawal Arpita et al: "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012 pp. 3320-3326, XP002780313.
Applicant: Case Western Reserve University; "Cancer Immunotherapy Using Virus Particles"; European Patent Application No. 21201960.8; Extended European Search Report dated Jan. 19, 2022; 11 pgs.
Brennan Frank R et al: "Cowpea mosaic virus as a vaccine carrier of heterologous antigens", Molecular Biotechnology, vol. 17, No. 1, Jan. 2001 (Jan. 2001), pp. 15-26, XP002780312, ISSN: 1073-6085.
Gonzalez Maria Jet al: "Interaction of Cowpea Mosaic Virus (CPMV) Nanoparticles with Antigen Presenting Cells In Vitro and In Vivo", Plos One, vol. 4, No. 11, Nov. 2009 (Nov. 2009), XP002780311, ISSN: 1932-6203.
Patrick h. Iizotte: "Novel approaches to targeting innate immunity for cancer immunotherapy", Proquest Dissertations Publishing, May 2015 (May 2015), XP002780316, Retrieved from the Internet: URL:https://search.proquest.com/docview/1695832154?pq-origsite=gscholar [retrieved on Apr. 19, 2018].
Saunders Ket Al: "Efficient generation of cowpea mosaicvirus empty virus-like particles by the proteolytic processing of precursors in insect cells and plants", Virology, Elsevier, Amsterdam, NL, vol. 393, No. 2, Oct. 25, 2009 (Oct. 25, 2009), pp. 329-337, XP026691170, ISSN: 0042-6822, DOI: 10.1016/J.VIROL.2009.08.023 [retrieved on Sep. 5, 2009].
Czapar, Anna et al. Tobacco Mosaic Virus Delivery of Phenanthriplatin for Cancer therapy. American Chemical Society. Nano 2016 (10) pp. 4119-4126 (Year: 2016).
Le, Duc et al. Biodistribution of Filamentous Plant Virus Nanoparticles: Pepino Mosaic Virus versus Potato Virus X. Biomacromolecules 219 Jan. 14; 20(a): pp. 469-477. (Year 2019).
Le, Duc et al. Chemical addressability of potoato virus X for its applications in bio/nanotechnology. El Sevier. Journal of Structural Biology 200 (2017). pp. 360-368. (Year: 2017).
Le, Duc et al. Potato virus X, a filamentous plant viral nanoparticle for doxorubicin delivery in cancer therapy. Royal Society of Chemistry. Nanoscale, 2017 (9). pp. 2348-2357. (Year 2017).
Nicole F. Steinmetz, U.S. Appl. No. 16/998,210, filed Aug. 7, 2020; Non-Final OA dated Dec. 7, 2022.
Tran, Hong Hanh. Developing a plant virus-based expression system for the expression of vaccines against Porcine Reproductive and Respiratory Syndrome Virus. Western Graduate & Postdoctoral Studies. Electronic Thesis and Dissertation Repository. (Year: 2017).
Bruckman et al. (Nano Letters. Mar. 2014; 14: 1551-1558).
Mitoxantrone. Drug Bank Online. Website. https://go.drugbank.com/drugs/DB01204. (Accessed Dec. 15, 2022) (Year: 2022).
Nicole F.Steinmetz; U.S. Appl. No. 16/597,509, filed Oct. 9, 2019; Non-Final Office Action, dated Dec. 27, 2022; 12 pgs.

(56) References Cited

OTHER PUBLICATIONS

Nicole F.Steinmetz; U.S. Appl. No. 16/759,652, filed Apr. 27, 2020; Final Office Action, dated Dec. 12, 2022; 15 pgs.
Nicole F.Steinmetz; U.S. Appl. No. 17/522,182, filed Nov. 9, 2021; Non-Final Office Action, dated Jan. 5, 2023; 27 pgs.
Nicole F.Steinmetz; U.S. Appl. No. 17/677,147, filed Feb. 22, 2022; Non-Final Office Action, dated Jan. 13, 2023; 22 pgs.
Pellico et al. (Contrast Media and Molecular Imaging. 2019; Article ID 1845637: 1-13).
Royston et al. (Journal of Colloidal and Interface Science. 2009; 332: 402-407).
Tamoxifen. Drug Bank Online. Website. https://go.drugbank.com/drugs/DB00675. (Accessed: Dec. 15, 2022) (Year: 2022).
Temming et al. (bioconjugate Chemistry. 2006; 17: 1385-1394).
Xiao et al. (International Journal of Molecular Medicine. 2016; 38: 1319-326).
Zhang et al. (Theranostics. 2018; 8 (9): 2521-2548).

\* cited by examiner

Figs. 3A-F

PLANT VIRAL RNA DELIVERY NANOPARTICLES AND USES THEREOF

RELATED APPLICATION

This application claims priority from U.S. Provisional Application No. 62/951,143, filed Dec. 20, 2019, the subject matter of which is incorporated herein by reference in its entirety.

TECHNICAL FIELD

This application relates to siRNA-loaded icosahedral-shaped plant virus nanoparticles and to their use in compositions for treating cancer.

BACKGROUND

Small regulatory RNA therapeutics, such as siRNA, have wide ranging applications in the regulation of cell protein expression. Gene silencing with siRNA holds tremendous promise in cancer therapy and beyond; synthetic siRNAs can be designed to target in principle any gene of interest, therefore enabling downregulation of genes involved in cell proliferation, epithelial-mesenchymal transition, or drug resistance. However, to make a clinical impact, a delivery strategy is required, because 'naked' siRNA are not stable in plasma, not targeted, and their negative charge impairs cell uptake.

Proposed siRNA delivery platforms have advantages and disadvantages. While mammalian viruses have been developed for gene therapy, these viruses have drawbacks such as possible adverse effects as a result of gene integration and their inherent immunogenicity. While non-viral systems generally offer safety, they do not match the effectiveness of viral delivery systems, as they can be instable in biological media leading to aggregation and/or premature cargo release. Therefore, there remains a continued need for the development of efficient gene delivery vehicles.

Plant-virus based-nanotechnologies provide an exciting alternative to the more traditional and more frequently exploited synthetic nanoparticles. Plant viruses, or viruses in general, can be considered as nature's delivery vehicles; viruses are designed to penetrate cells and deliver cargo. While mammalian viruses have been used to deliver genes for nucleic acid therapy, plant viruses offer a safer alternative due to their inability to infect or replicate in mammalian cells. Like other biologics, plant virus-based nanoparticles can be manufactured through a variety of homologous and heterologous expression systems at high yields and with high quality control and assurance. Plant viruses are monodisperse and many of their structures are known to near atomic resolution; therefore enabling structure-based design of high precision nanodrug delivery systems.

SUMMARY

Embodiments described herein relate to RNAi construct-loaded icosahedral-shaped plant virus nanoparticles, pharmaceutical compositions comprising these nanoparticles, and methods for treating cancers in a subject using these RNAi construct-loaded nanoparticles.

In some embodiments, a nanoparticle includes an icosahedral-shaped plant virus particle, an RNAi construct, and an endolysosomal release agent, wherein the RNAi construct is noncovalently loaded within the icosahedral-shaped plant virus particle. The icosahedral-shaped plant virus particle can belong to the Bromoviridae family. In some embodiments, the icosahedral-shaped plant virus particle is a cowpea chlorotic mottle virus (CCMV) virus particle. In some embodiments, the RNAi construct is a siRNA, such as an siRNA targeting the forkhead box transcription factor (FOXA1) oncogene.

The endolysosomal release agent can be linked to the exterior surface of the icosahedral-shaped plant virus particle. In some embodiments, the endolysosomal release agent can include an L17E M-lycotoxin peptide.

Another embodiment relates to a method of treating cancer in a subject. The method includes administering to the subject a therapeutically effective amount of a nanoparticle that includes an icosahedral-shaped plant virus particle, an RNAi construct, and an endolysosomal release agent, wherein the RNAi construct is encapsulated within the icosahedral-shaped plant virus particle. The nanoparticle can be administered to the subject systemically. In some embodiments, the cancer is selected from the group consisting of hormone dependent breast cancer and hormone dependent prostate cancer.

The icosahedral-shaped plant virus particle can belong to the Bromoviridae family. In some embodiments, the icosahedral-shaped plant virus particle is a cowpea chlorotic mottle virus (CCMV) virus particle. In some embodiments, the RNAi construct is a siRNA, such as a siRNA targeting the forkhead box transcription factor (FOXA1) oncogene.

In some embodiments, the endolysosomal release agent can be linked to the exterior surface of the icosahedral-shaped plant virus particle. The endolysosomal release agent can include a L17E M-lycotoxin peptide.

In some embodiments, the method can further include administering a therapeutically effective amount of an additional anticancer agent or therapy to the subject. The additional cancer agent can include an antitumor agent and/or an anti-hormonal agent. The additional anticancer therapy can include radiation therapy, brachytherapy, and/or ablation therapy.

Yet another embodiment relates to method of treating hormone dependent breast cancer in a subject. The method includes administering to the subject a therapeutically effective amount of nanoparticle comprising an CCMV virus particle, an siRNA targeting the forkhead box transcription factor (FOXA1) oncogene, and one or more endolysosomal release agents comprising a L17E M-lycotoxin peptide, wherein the RNAi construct is encapsulated within the CCMV virus particle.

DETAILED DESCRIPTION

Figure 1A:
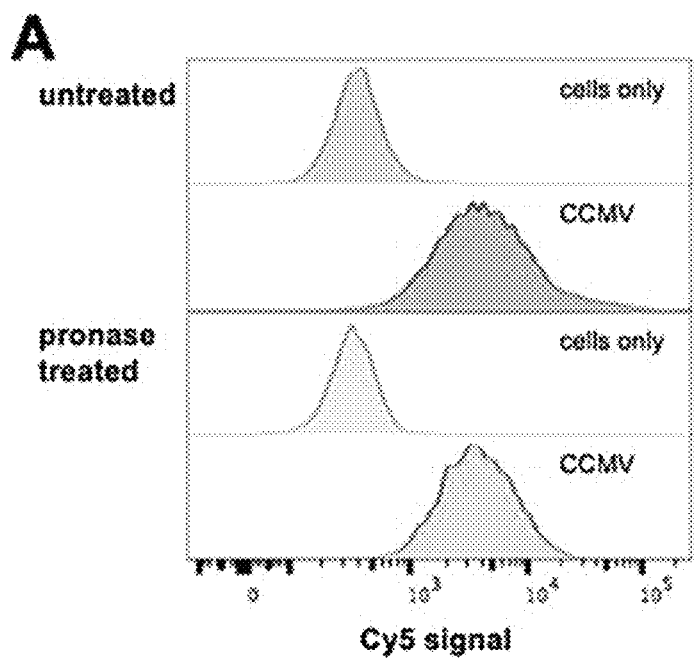
FIGS. 1(A-D) are graphs and microscopic images showing (A) Flow cytometry was used to assess the uptake of CCMV-Cy5 in HeLa cells after incubation at 37° C. for 6 h. Following incubation, cells were treated with and without pronase to remove any loosely bound particles from the cell. (B) mean fluorescence intensity. (C,D) Confocal microscopy of HeLa cells (C), and HeLa cells with CCMV-Cy5 particles (D). Scale bar=25 μm.

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

The terms "comprise," "comprising," "include," "including," "have," and "having" are used in the inclusive, open sense, meaning that additional elements may be included. The terms "such as", "e.g.,", as used herein are non-limiting and are for illustrative purposes only. "Including" and "including but not limited to" are used interchangeably.

The term "or" as used herein should be understood to mean "and/or", unless the context clearly indicates otherwise.

The terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

The terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

The term "nanoparticle" refers to any particle having a diameter of less than 1000 nanometers (nm). In general, the nanoparticles should have dimensions small enough to allow their uptake by eukaryotic cells. Typically, the nanoparticles have a longest straight dimension (e.g., diameter) of 200 nm or less. In some embodiments, the nanoparticles have a diameter of 100 nm or less. Smaller nanoparticles, e.g., having diameters of 50 nm or less, e.g., about 1 nm to about 30 nm or about 1 nm to about 5 nm, are used in some embodiments.

The phrases "parenteral administration" and "administered parenterally" are art-recognized terms and include modes of administration other than enteral and topical administration, such as injections, and include, without limitation, intratumoral, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The phrases "systemic administration," "administered systemically," "peripheral administration" and "administered peripherally" as used herein mean the administration of a compound, agent or other material other than directly into a specific tissue, organ, or region of the subject being treated (e.g., tumor site), such that it enters the animal's system and, thus, is subject to metabolism and other like processes, for example, subcutaneous administration.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a sufficient amount of the composition used in the practice of the invention that is effective to provide effective treatment in a subject, depending on the compound being used. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

A "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder.

A "therapeutic" treatment is a treatment administered to a subject who exhibits signs of pathology of a disease or disorder for the purpose of diminishing or eliminating those signs.

"Pharmaceutically acceptable carrier" refers herein to a composition suitable for delivering an active pharmaceutical ingredient, such as the composition of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

The term "imaging agent" or "imaging moiety" can refer to a biological or chemical moiety capable being linked and/or conjugated directly or indirectly to siRNA-loaded plant viral nanoparticles described herein and that may be used to detect, image, and/or monitor the presence and/or progression of a cell cycle, cell function/physiology, condition, pathological disorder and/or disease.

The term "polypeptide" or "peptide" is meant to refer to any polymer preferably consisting essentially of any of the 20 natural amino acids regardless of its size. Although the term "protein" is often used in reference to relatively large proteins, and "peptide" is often used in reference to small polypeptides, use of these terms in the field often overlaps. The term "polypeptide" refers generally to proteins, polypeptides, and peptides unless otherwise noted. Peptides described herein will be generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis.

The terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

Embodiments described herein relate to an RNAi construct-loaded plant virus nanoparticle. The nanoparticle includes an icosahedral shaped plant virus particle or virus like particle (VLP), an RNAi construct, such as siRNA, and one or more endolysosomal release agents, wherein the RNAi construct is encapsulated within the icosahedral shaped plant virus or VLP. It has been shown using transmission electron microscopy (TEM) imaging that icosahedral plant viral particles can be effectively loaded with gene silencing siRNAs, thereby producing structurally sound icosahedral nanoparticles capable of RNAi construct delivery. For example, the icosahedral plant virus cowpea chlorotic mottle virus (CCMV) was shown to be effectively loaded with siRNAs targeting the forkhead box transcription factor (FOXA1) oncogene.

In some embodiments, the nanoparticles can be based on icosahedral-shaped plant virus particles and include plant virus nanoparticles and/or plant virus-like particles. Plant virus particles preferably grow in plants, have the advantages of being readily cultivated, and are unlikely to cause infection when used in vivo in a subject. The icosahedral-shaped plant virus particles or virus-like particle can be nonreplicating and noninfectious when administered to a subject to avoid infection of the subject, and thus can be regarded as safe from a human health and agricultural perspective. In planta production prevents endotoxin contamination that may be a byproduct of other virus or virus-like particle systems, for example those virus-like particles derived from E. coli. The icosahedral-shaped virus particles or virus-like particles are scalable, stable over a range of temperatures (4-60° C.) and solvent:buffer mixtures.

An icosahedral-shaped plant virus is a small spherical virus that primarily infects plants, is non-enveloped and composed of capsid proteins that can self-assemble into well-organized icosahedral three-dimensional (3D) nanoscale multivalent architectures with high monodispersity and structural symmetry. Icosahedral-shaped plant viruses also include an exterior surface and interfaces between coat protein (CP) subunits that can be manipulated to allow for controlled self-assembly, and multivalent ligand display of nanoparticles or molecules for varied applications.

In some embodiments, the icosahedral-shaped plant virus belongs to a specific virus family, genus, or species. Examples of icosahedral-shaped plant viruses for use in a siRNA-loaded plant virus nanoparticle described herein can be derived from the virus families Secoviridae, Geminiviridae, Luteoviridae, Bromoviridae, Phycodnaviridae, and Picornaviridae.

For example, in some embodiments, the icosahedral-shaped plant virus belongs to the Bromoviridae family. The Bromoviridae family includes the genus Bromovirus, Ilarvirus, Anulavirus, Oleavirus, and Cucumovirus. In some embodiments, the icosahedral-shaped plant virus belongs to the genus Bromovirus. The Bromovirus genus includes the species Brome mosaic virus (BMV), Broad Bean Mottle Virus (BBMV), Melandrium Yellow Fleck Virus (MYFV), Spring beauty latent virus (SBLV), Cassia yellow blotch virus (CYBV) and Cowpea Chlorotic Mottle Virus (CCMV).

In certain embodiments, the icosahedral-shaped plant virus belongs to the CCMV species. CCMV has a capsid constructed by 180 identical protein subunits each with a primary structure of 190 amino acid residues. There are three subunits are distributed over the virus coat, A, B, and C. The A subunits are arranged in pentamers and the B and C subunits are together arranged in hexamers. The virus coat is built up from 12 pentamers and 20 hexamers. Inside the capsid lies the (+)ssRNA genome consisting of around 3000 nucleotides.

In some embodiments, the icosahedral-shaped plant virus belongs to the Secoviridae family, which together with mammalian picornaviruses belong to the order of the Picornavirales. Secoviridae family plant viruses are relatively small having a diameter of about 30 nm, non-enveloped, positive-stranded RNA viruses with an icosahedral capsid. In some embodiments, the plant virus particles are selected from the Comovirinae virus subfamily of Secoviridae. Exemplary Comovirinae subfamily viruses for use in a method described herein can include Cowpea mosaic virus (CPMV), Broad bean wilt virus 1, and Tobacco ringspot virus. In certain embodiments, the plant virus or plant virus-like particles are from the genus *Comovirus*. A preferred example of a *Comovirus* is the CPMV or CPMV-like virus particles. The immune stimulating ability of CPMV is derived from its highly organized 3D protein architecture with its encapsulated nucleic acid and an intrinsic immune cell tropism. In some embodiments, the plant virus-like particle is an empty cowpea mosaic virus-like particle (eCPMV).

In one embodiment, CCMV can be propagated by mechanical inoculation using 5-10 μg of CCMV per leaf of cowpea plants, California Blackeye No. 5 (*Vigna unguiculata*). To isolate the virus, infected leaf material can be harvested 8 weeks post infection and purified. In another embodiment CPMV can be propagated in and purified from *Vigna unguiculata* plants with yields of 50-100 mg virus/100 g of infected leaves. In another embodiment, icosahedral plant virus, such as CCMV or CPMV, can be produced using an *E. coli* expression system.

In some embodiments, an RNAi construct is loaded into the interior of the icosahedral-shaped plant virus particle. In an example, siRNA encapsulation within an icosahedral-shaped plant virus particle or virus-like particle is achieved using pH- and salt-controlled, dis- and assembly methods to yield CCMV loaded with siRNA targeting the oncogene FOXA1, where the siRNA are added at a 6:1 (w/w) ratio (see FIG. 2A) to form about 30 nm-sized icosahedral particles (FIGS. 2B,C). In certain embodiments, about 2-3 μM siRNAs can be encapsulated by the icosahedral-shaped plant virus particle or virus-like particle.

RNAi constructs loaded into an icosahedral-shaped plant virus particle or virus-like particle for use in a composition or method described herein can comprise double stranded RNA that can specifically block expression of a target gene. As used herein, the term "RNAi construct" is a generic term used throughout the specification to include small interfering RNAs (siRNAs), hairpin RNAs, and other RNA species, which can be cleaved in vivo to form siRNAs.

"RNA interference" or "RNAi" is a term initially applied to a phenomenon observed in plants and worms where double-stranded RNA (dsRNA) blocks gene expression in a specific and post-transcriptional manner. As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a decrease or diminishment in the level of expression of a gene when compared to the level in the absence of RNAi constructs. The term "expression", as used here, means the overall flow of information from a gene to produce a gene product (typically a protein, optionally post-translationally modified or a functional/structural RNA).

In some embodiments, the RNAi constructs loaded into a icosahedral-shaped plant virus particle or virus like particle can decrease the expression level of a therapeutic target in a cell of a subject in need thereof using gene silencing. For example, it was shown using confocal microscopy successful gene silencing mediated by an icosahedral-shaped plant viral siRNA delivery vector described herein (see FIG. 3A-F).

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

Thus, embodiments tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, a modified ribonucleotide can be introduced by in vitro enzymatic or organic synthesis.

Methods of chemically modifying RNA molecules can be adapted for modifying RNAi constructs (see for example, Nucleic Acids Res, 25:776-780; J Mol Recog 7:89-98; Nucleic Acids Res 23:2661-2668; Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules described herein can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Proc Nal Acad Sci USA, 98:9742-9747; EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer to produce a dicer-substrate siRNA. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides, also referred to as 21 to 23-mer designs as the length of the oligonucleotide is usually denoted by "-mer" (from Greek meros, "part").

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In some embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Genes Dev, 2002, 16:948-58; Nature, 2002, 418:38-9; RNA, 2002, 8:842-50; and Proc Natl Acad Sci, 2002, 99:6047-52. Preferably, such hairpin RNAs are engineered in cells or in an animal to ensure continuous and stable suppression of a desired gene. It is known in the art that siRNAs can be produced by processing a hairpin RNA in the cell.

In another embodiment, an icosahedral-shaped plant virus particle or virus-like particle can be loaded with a gene silencing nucleotide agent that reduces or inhibits expression of a target gene such as but not limited to an antisense oligonucleotides (ASOs). Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

The binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their delivery to a cell through encapsulation in an icosahedral-shaped plant virus particle or virus-like particle allows the degradation of the mRNA encoding a specific protein. Accordingly, antisense oligonucleotides decrease the expression and/or activity of a particular protein (e.g., an oncoprotein).

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc.

Oligonucleotides described herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209), methylphosphonate oligonucleotides can be prepared by use of controlled pore glass polymer supports (*Proc Nal Acad Sci* 85:7448-7451)

The selection of an appropriate oligonucleotide can be performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

It was shown that icosahedral-shaped plant virus can, at least in part, become entrapped in the endolysosomal compartment of cancer cells. Thus, an icosahedral-shaped plant virus like particle loaded with an RNAi construct can be appended with one or more endolysosomal release agents to facilitate protein expression in cancer cells by disrupting endolysosomal membranes. Endolysosomal release agents for use in a composition described herein can include any agent capable of enhancing cancer cell uptake and intracellular trafficking. In some embodiments, the endolysosomal agent, can facilitate endolysosomal release of RNAi construct entrapped in the endolysosomal compartment into the cytoplasm of cancer cells of the subject, thereby overcoming the need for co-delivery of a transfection agent, such as Lipofectamine.

In some embodiments, the one or more endolysosomal release agents can include a cell penetrating peptide (CPP), also known as a protein transduction domain (PTD). In addition to enhancing endolysosomal release, CPPs for use in a composition described herein can facilitate uptake of the icosahedral-shaped plant virus like particle into a cancer cell where the loaded RNAi construct can provide efficient gene silencing in cancer cells.

The number of endolysosomal release agents appended to an icosahedral-shaped plant virus particle may affect (e.g., increase) the endolysosomal release and/or uptake of the nanoparticle by a desired cell. In some embodiments, an icosahedral-shaped plant virus particle or virus like particle loaded with an RNAi construct as described herein can display about 10 to about 100 cell penetrating peptides per particle. In certain embodiments, an icosahedral-shaped plant virus particle or virus like particle loaded with an RNAi construct can display about 30 endolysosomal release agents per particle.

Endolysosomal release agents can be coupled to an RNAi construct loaded icosahedral-shaped plant virus particle or virus like particle either directly or indirectly (e.g., via a linker group). In some embodiments, the endolysosomal release agents can be covalently conjugated to coat proteins of the icosahedral-shaped plant virus particle or virus like particle. The covalent link can include a peptide bond or a labile bond (e.g., a bond readily cleavable or subject to chemical change in the interior target cell environment).

In some embodiments, an endolysosomal release agent is conjugated to a coat protein of an icosahedral-shaped plant virus particle or virus like particle via a linker. In an exemplary embodiment, peptide endolysosomal release agents can be synthesized with a C-terminal amide or Gly-Gly-Cys linker allowing for conjugation of the peptide endolysosomal release agent to surface lysines of a CCMV virus particle using an SM(PEG)4 linker.

In some embodiments, CCPs can include at least one transport peptide sequence that allows the icosahedral-shaped plant virus particle or virus like particle to penetrate into a cell, such as a cancer cell. Examples of transport sequences that can be used in accordance with the present invention include a TAT-mediated protein delivery sequence (GRKKRRQRRRPQ) (SEQ ID NO: 1) (Vives (1997) 272: 16010-16017), polyargine sequences (Wender et al. 2000, PNAS 24: 13003-13008) and antennapedia (Derossi (1996) J. Biol. Chem. 271: 18188-18193). Other examples of known transport peptide moieties, subdomains and the like are described in, for example, Canadian patent document No. 2,301,157 (conjugates containing homeodomain of antennapedia) as well as in U.S. Pat. Nos. 5,652,122, 5,670, 617, 5,674,980, 5,747,641, and 5,804,604, all of which are incorporated herein by reference in their entirety. Such transport moieties include conjugates containing amino acids of Tat HIV protein; herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

CPPs are short peptides (<30 amino acids long) that are able to penetrate biological membranes and drive the internalization of a bioactive cargo in cells. CPPs for use in a can include positively and negatively charged, amphipathic (primary or secondary) and non-amphipathic CPPs. CPPs can be placed into the following three main groups: PTDs (Tat, Penetratin, etc.); model peptides (R9, KLAK); and designed peptides (Pep-1, sequence: KETWWETWWTEWS-QPKKKRKV) (SEQ ID NO: 2). A review of cell-penetrating peptides can be found in Kalafatovic and Giralt, Molecules, 22(11), 1929 (2017) incorporated by reference in its entirety.

Penetratin (RQIKIWFQNRRMKWKK) (SEQ ID NO: 3) is a CPP, of which the first 16 amino acids are derived from the third alpha helix of the Antennapedia protein. Penetratin has been shown to enable proteins (made as fusion proteins) to cross cellular membranes (PCT international publication number WO 99/11809, incorporated by reference in its entirety). Similarly, HIV Tat protein was shown to be able to cross cellular membranes (Frankel A. D. et al., Cell, 55: 1189).

In some embodiments, the endolysosomal release agent can include endosomolytic peptide CPPs derived from the cationic and membrane-lytic spider venom peptide M-lycotoxin (see Akishiba et al. Nature Chemistry, 9, 751-761 (2017)). These delivery peptides were developed by introducing one or two glutamic acid residues into the hydrophobic face. In a particular embodiment, the transport moiety includes the M-lycotoxin peptide having the substitution of leucine by glutamic acid (L17E). L17E has been shown to promote cell uptake by micropinocytosis. Moreover, the addition of L17E to CCMV particles loaded with siRNA targeting an oncogene was shown to increase gene silencing efficacy. In an exemplary embodiment, the L17E peptide has the amino acid sequence

IWLTALKFLGKHAAKHEAKQQLSKL. (SEQ ID NO: 4)

In additional embodiments, the CPPs can include polypeptides having a basic amino acid rich region covalently linked to the inhibiting peptide. As used herein, the term "basic amino acid rich region" relates to a region of a protein with a high content of the basic amino acids such as arginine, histidine, asparagine, glutamine, lysine. A "basic amino acid rich region" may have, for example 15% or more (up to 100%) of basic amino acids. In some instance, a "basic amino acid rich region" may have less than 15% of basic amino acids and still function as a transport agent region. More preferably, a basic amino acid region will have 30% or more (up to 100%) of basic amino acids.

The CPPs may further include a proline rich region. As used herein, the term proline rich region refers to a region of a polypeptide with 5% or more (up to 100%) of proline in its sequence. In some instance, a proline rich region may have between 5% and 15% of prolines. Additionally, a proline rich region refers to a region, of a polypeptide containing more prolines than what is generally observed in naturally occurring proteins (e.g., proteins encoded by the human genome). Proline rich regions of the present invention can function as a transport agent region.

Other CPPs that have been tested in other contexts, (i.e., to show that they work through the use of reporter sequences), are known. One transport peptide, AAVLLPVLLAAP (SEQ ID NO: 5), is rich in proline. This transport made as a GST-MTS fusion protein and is derived from the h region of the Kaposi FGF signal sequence (Royas et al. (1998) Nature Biotech. 16: 370-375). Another example is the sperm fertiline alpha peptide, HPIQIAAFLARIPPISSIGTCILK (SEQ ID NO: 6) (See Pecheur, J. Sainte-Marie, A. Bienvenuje, D. Hoekstra. 1999. J. Membrane Biol. 167: 1-17).

Additional CPPs for use in a composition described herein can include a GGRRRRRRRRR-amide (KTG Pharmaceuticals, Inc.), a cell-permeant miniature protein (CPMP) that embodies a penta-Arg motif, and an amphipathic peptide,

GGACGAGGACGAGCACUUC. (SEQ ID NO: 7)

In some embodiments, the icosahedral-shaped plant virus particle or virus like particle can be non-covalently linked to a transfection agent. An example of a non-covalently linked polypeptide transfection agent is the Chariot protein delivery system (See U.S. Pat. No. 6,841,535; Morris et al. (1999) J. Biol. Chem. 274(35):24941-24946; and Morris et al. (2001) Nature Biotech. 19:1173-1176), all herein incorporated by reference in their entirety.

The Chariot protein delivery system includes a peptide transfection agent that can non-covalently complex with the surface of the RNAi construct loaded icosahedral-shaped plant virus particle or virus like particle. Upon cellular internalization, the transfection agent dissociates from the nanoparticle. The complex of the Chariot transfection peptide and the RNAi construct loaded icosahedral plant virus particle or VLP can be delivered to and internalized by mammalian cells allowing for higher dosages of therapeutics to be delivered to the site of pathology.

Gene silencing has been shown to be an effective strategy in the treatment of cancer. For example, gene silencing can be used to inhibit cell proliferation and/or induce G0/G1 arrest in cancer cells. Therefore, some embodiments described herein also relate to methods of treating cancer in a subject in need thereof by administering to the subject a therapeutically effective amount of RNAi construct-loaded plant virus nanoparticle. The nanoparticle includes an icosahedral shaped plant virus particle or virus like particle (VLP) and an oncogene targeted RNAi construct, wherein the RNAi construct is encapsulated within the icosahedral shaped plant virus or VLP. In some embodiments, a targeting moiety can also be attached to the RNAi construct loaded icosahedral plant virus nanoparticle. In certain embodiments, the targeting moiety can include the M-lycotoxin peptide (L17E). In some embodiments, the RNAi construct can include an oncogene targeted siRNA. In an exemplary embodiment, the oncogene targeted siRNA includes a FOXA1 oncogene targeting siRNA.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression.

The cancers treated by a method described herein can include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, glioblastoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytoma and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, fallopian tube cancer, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In some embodiments, the cancer is selected from the group consisting of breast cancer and prostate cancer. In particular embodiments, the cancer is a hormone-dependent breast or prostate cancer.

In some embodiments, the subject being administered a therapeutically effective amount of an RNAi construct-loaded icosahedral-shaped plant virus nanoparticle is a subject who has been identified as having cancer. As is known to those skilled in the art, there are a variety of methods of identifying (i.e., diagnosing) a subject who has cancer. For example, diagnosis of cancer can include one or more of a physical exam, laboratory tests, imaging analysis, and biopsy. After cancer is diagnosed, a variety of tests may be carried out to look for specific features' characteristic of different types and or the extent of cancer in the subject. These tests include, but are not limited to, bone scans, X-rays, immunophenotyping, flow cytometry, and fluorescence in situ hybridization testing. For example, typical methods of diagnosing breast cancer can include, but are not limited to, a physical exam, digital mammogram, breast MRI, breast ultrasound, stereotactic core and/or open tumor biopsy, as well as lab tests to determine if the tumor tissue expresses estrogen and progesterone receptors. Typical methods of diagnosing prostate cancer can include, but are not limited to, physical digital rectal examination a serum prostate-specific antigen (PSA) test, transrectal ultrasound, MRI fusion biopsy, Prostate Cancer gene 3 (PCA3) assay, PCA3 test, prostatic biopsy and histologic analysis.

In some embodiments, the RNAi construct-loaded icosahedral-shaped plant virus nanoparticle is used to target cancer cells or cancer tissue in a subject. As used herein, targeting cancer tissue includes the ability of the anti-cancer virus particles to reach and preferably accumulate at site of cancer after being administered to the subject, for example, where the anti-cancer virus particles are systemically administered to a subject. The ability of RNAi construct-loaded icosahedral-shaped plant virus nanoparticle to target cancer tissue is supported by the in vitro cell uptake studies carried out by the inventors. See International Patent Publication WO2013/181557, the disclosure of which is incorporated herein by reference. While not intending to be bound by theory, it appears that icosahedral-shaped plant virus particles are drawn to the leaky vasculature caused by the angiogenesis associated with rapid tumor growth, and this leaky vasculature encourages entry for anti-cancer plant virus particles through small pores, thereby delivering the RNAi construct-loaded icosahedral-shaped plant virus nanoparticles to the cancer cells. As a result of this preferential accumulation, embodiments of the invention can deliver about 10%, about 20%, about 30%, about 40%, or even about 50% or more of the injected dose to tumor tissue.

In some embodiments, the administration of the nanoparticles can be proximal to a tumor in the subject or directly to the tumor site to provide a high local concentration of the RNAi construct-loaded icosahedral-shaped plant virus nanoparticle thereof in the tumor microenvironment (TME). In certain embodiments, the addition of one or more endolysosomal release agents, such as a CPP, can allow for endolysosomal escape of the RNAi construct-loaded icosahedral-shaped plant virus nanoparticle thereby increasing gene silencing efficiency in cancer cells.

In some embodiments, a coating can be added to the exterior of the RNAi construct-loaded icosahedral-shaped plant virus nanoparticle to improve bioavailability. Administering plant virus particles to a subject can sometimes generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Accordingly, in some embodiments it may be preferable to modify the exterior of the plant virus particle or take other steps to decrease the immune response. For example, an immunosuppressant compound can be administered to decrease the immune response. More preferably, the RNAi construct-loaded icosahedral-shaped plant virus nanoparticle can be modified to decrease its immunogenicity. Examples of methods suitable for decreasing immunity include attachment of anti-fouling (e.g., zwitterionic) polymers, glycosylation of the virus carrier, and PEGylation.

In some embodiments, the immunogenicity of RNAi construct-loaded icosahedral-shaped plant virus nanoparticle is decreased by PEGylation. PEGylation is the process of covalent attachment of polyethylene glycol (PEG) polymer chains to a molecule such as a filamentous plant virus carrier. PEGylation can be achieved by incubation of a reactive derivative of PEG with the plant virus nanoparticle exterior. The covalent attachment of PEG to the RNAi construct-loaded icosahedral-shaped plant virus nanoparticle can "mask" the agent from the host's immune system, and reduce production of antibodies against the carrier. PEGylation also may provide other benefits. PEGylation can be used to vary the circulation time of the RNAi construct-loaded icosahedral-shaped plant virus nanoparticle.

The first step of PEGylation is providing suitable functionalization of the PEG polymer at one or both terminal positions of the polymer. The chemically active or activated derivatives of the PEG polymer are prepared to attach the PEG to the anti-lymphoma virus particle. There are generally two methods that can be used to carry out PEGylation; a solution phase batch process and an on-column fed-batch process. The simple and commonly adopted batch process involves the mixing of reagents together in a suitable buffer solution, preferably at a temperature between 4 and 6° C., followed by the separation and purification of the desired product using a chromatographic technique.

In some embodiments, a method of treating cancer described herein can further include can include administering an additional therapeutic or cancer therapy to the subject. A "cancer therapeutic" or "cancer therapy", as used herein, can include any agent or treatment regimen that is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of an animal with cancer. Cancer therapeutics can include one or more therapies such as, but not limited to, chemotherapies, radiation therapies, hormonal therapies, and/or biological therapies/immunotherapies. A reduction, for example, in cancer volume, growth, migration, and/or dispersal in a subject may be indicative of the efficacy of a given therapy.

In some embodiments, the method can include the step of administering a therapeutically effective amount of an additional anticancer therapeutic agent to the subject. Additional anticancer therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA. In some embodiments, cytotoxic compounds are included in an anticancer agent described herein. Cytotoxic compounds include small-molecule drugs such as doxorubicin, methotrexate, vincristine, and pyrimidine and purine analogs, referred to herein as antitumor agents.

The additional anticancer therapeutic agent can include an anticancer or an antiproliferative agent that exerts an antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and *vinca* alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Examples of anticancer therapeutic agents that can be administered in combination with a RNAi construct loaded icosahedral-shaped plant virus nanoparticle described herein include Taxol, Adriamycin, dactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine;

dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; temozolomide, teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Additional anticancer therapeutic agents for the treatment of prostate cancer include systemic chemotherapeutics. Typically for the treatment of prostate cancer, standard systemic chemotherapy begins with docetaxel (Docefrez, Taxotere) combined with a steroid called prednisone. Additional systemic chemotherapeutics can include cabazitaxel and mitoxantrone. For subjects identified as having metastatic hormone-sensitive prostate cancer, Abiraterone acetate and prednisone can be administered in combination.

In particular embodiments, an additional anti-prostate cancer therapeutic agent can include an androgen deprivation therapy (ADT) agent, such as but not limited to LHRH agonists, LHRH antagonists, anti-androgen agents, and combinations thereof.

Additional anticancer therapeutic agents for the treatment of hormone sensitive breast cancer can include ovarian suppression drugs such as goserelin and leuprolide, aromatase inhibitors such as anastrozole, letrozole and exemestane, selective estrogen receptor modulators (SERMs) such as tamoxifen, raloxifene and toremifene, other antiestrogen drugs such as fulvestrant.

In some embodiments, the anti-cancer therapy administered to the subject in addition to the RNAi construct loaded icosahedral-shaped plant virus nanoparticles can include the cancer ablation therapy. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, immunotherapy, and administration of immunotoxins.

In some embodiments, ablating the cancer includes immunotherapy of the cancer. Cancer immunotherapy is based on therapeutic interventions that aim to utilize the immune system to combat malignant diseases. It can be divided into unspecific approaches and specific approaches. Unspecific cancer immunotherapy aims at activating parts of the immune system generally, such as treatment with specific cytokines known to be effective in cancer immunotherapy (e.g., IL-2, interferon's, cytokine inducers). In contrast, specific cancer immunotherapy is based on certain antigens that are preferentially or solely expressed on cancer cells or predominantly expressed by other cells in the context of malignant disease (usually in vicinity of the tumor site). Specific cancer immunotherapy can be grouped into passive and active approaches.

In passive specific cancer immunotherapy substances with specificity for certain structures related to cancer that are derived from components of the immune system are administered to the patient. The most prominent and successful approaches are treatments with humanized or mouse/human chimeric monoclonal antibodies against defined cancer associated structures (such as Trastuzumab, Rituximab, Cetuximab, Bevacizumab, Alemtuzumab). The pharmacologically active substance exerts is activity as long as a sufficient concentration is present in the body of the patient, therefore administrations have to be repeated based on pharmacokinetic and pharmacodynamic considerations.

On the other hand, active specific cancer immunotherapy aims at antigen-specific stimulation of the patient's immune system to recognize and destroy cancer cells. Active specific cancer immunotherapy therefore, in general, is a therapeutic vaccination approach. There are many types of cancer vaccine approaches being pursued, such as vaccination with autologous or allogeneic whole tumor cells (in most cases genetically modified for better immune recognition), tumor cell lysates, whole tumor associated antigens (produced by means of genetic engineering or by chemical synthesis), peptides derived from protein antigens, DNA vaccines encoding for tumor associated antigens, surrogates of tumor antigens such as anti-idiotypic antibodies used as vaccine antigens, and the like. These manifold approaches are usually administered together with appropriate vaccine adjuvants and other immunomodulators in order to elicit a quantitatively and qualitatively sufficient immune response (many novel vaccine adjuvant approaches are being pursued in parallel with the development of cancer vaccines). Another set of cancer vaccine approaches relies on manipulating dendritic cells (DC) as the most important antigen presenting cell of the immune system. For example, loading with tumor antigens or tumor cell lysates, transfection with genes encoding for tumor antigens and in vivo targeting are suitable immunotherapies that can be used together with the RNAi construct loaded icosahedral-shaped plant virus nanoparticles of the invention for cancer treatment.

In some embodiments, ablating the cancer includes administering a therapeutically effective amount of radiotherapy (RT) to the subject. In some embodiments, RT is administered prior to administration of the RNAi construct loaded icosahedral-shaped plant virus nanoparticles. In some embodiments, administering to the cancer, (e.g., at a tumor site) a therapeutically effective amount of a RNAi construct loaded icosahedral-shaped plant virus nanoparticle to the subject in combination with administering radiotherapy to the subject can result in an increase in tumor infiltrating lymphocytes (TILs), such as tumor infiltrating neutrophils (TINs) at the tumor site of the subject.

Radiotherapy uses high-energy rays to treat disease, usually x-rays and similar rays (such as electrons). Radiotherapy administered to a subject can include both external and internal. External radiotherapy (or external beam radiation) aims high-energy x-rays at the tumor site including in some cases the peri-tumor margin. External radiotherapy typically includes the use of a linear accelerator (e.g., a Varian 2100C linear accelerator). External radiation therapy can include three-dimensional conformal radiation therapy (3D-CRT), image guided radiation therapy (IGRT), intensity modulated radiation therapy (IMRT), helical-tomotherapy, photon beam radiation therapy, proton beam radiation therapy, stereotactic radiosurgery and/or sterotactic body radiation therapy (SBRT).

Internal radiotherapy (brachytherapy) involves having radioactive material placed inside the body and allows a higher dose of radiation in a smaller area than might be possible with external radiation treatment. It uses a radiation source that is usually sealed in an implant. Exemplary implants include pellets, seeds, ribbons, wires, needles, capsules, balloons, or tubes. Implants are placed in your body, very close to or inside the tumor. Internal radiotherapy can include intracavitary or interstitial radiation. During intracavitary radiation, the radioactive source is placed in a body cavity (space), such as the uterus. With interstitial radiation, the implants are placed in or near the tumor, but not in a body cavity.

In some embodiments, a checkpoint inhibitor can be further administered to eradicate suppressive regulatory T cells prior to RT. Exemplary checkpoint inhibitors can include CTLA4 and PD-1/PDL-1 inhibitors. The cytotoxic T-lymphocyte-associated antigen 4 (CTLA-4) and programmed death 1 (PD-1) immune checkpoints are negative regulators of T-cell immune function and inhibition of these targets, results in increased activation of the immune system. Therefore, in some embodiments, a checkpoint inhibitor administered to a subject can include a CTLA-4 and/or PD-1 inhibitor. For example, Ipilimumab, an inhibitor of CTLA-4, is approved for the treatment of advanced or unresectable melanoma. Nivolumab and pembrolizumab, both PD-1 inhibitors, are approved to treat patients with advanced or metastatic melanoma and patients with metastatic, refractory non-small cell lung cancer. In addition, the combination of ipilimumab and nivolumab has been approved in patients with BRAF WT metastatic or unresectable melanoma.

It has been shown that moderate magnetic nanoparticle hyperthermia (mNPH) treatment administered to a tumor can generate immune-based systemic resistance to tumor rechallenge. Therefore, in some embodiments, a therapeutically effective amount of a moderate magnetic nanoparticle hyperthermia (mNPH) treatment can be administered to the subject in combination with an RNAi construct loaded icosahedral-shaped plant virus nanoparticles and/or radiotherapy, wherein the mNPH is activated with an alternating magnetic field (AMF) to produce moderate heat. Without being bound by theory, it is believed that plant virus-like particle immune adjuvants, such as a plant virus nanoparticle and/or a mNPH, will combine with RT-induced generation of immunogenic cell death (ICD) to expand the tumor specific effector T cell population causing longer local and distant tumor remission.

A mNPH treatment can include the use of a magnetic iron oxide nanoparticle (IONP). Once administered to the subject intratumorally, the mNPH can, in some embodiments, be activated with an alternating magnetic field (AMF) to produce moderate heat (e.g., 43°/60° min) at the tumor site. In some embodiments, the RT is hypofractionated RT (HFRT) that delivers larger but fewer doses/fractions than typical RT therapies.

When used in vivo, the RNAi construct loaded icosahedral-shaped plant virus nanoparticles and/or additional anti-cancer therapeutic agents described herein can be administered as a pharmaceutical composition, comprising a mixture, and a pharmaceutically acceptable carrier. The RNAi construct loaded icosahedral-shaped plant virus nanoparticles may be present in a pharmaceutical composition in an amount from 0.001 to 99.9 wt %, more preferably from about 0.01 to 99 wt %, and even more preferably from 0.1 to 95 wt %.

The RNAi construct loaded icosahedral-shaped plant virus nanoparticles, or pharmaceutical compositions comprising these particles and/or additional anti-cancer agent, may be administered by any method designed to provide the desired effect. Administration may occur enterally or parenterally; for example orally, rectally, intracisternally, intravaginally, intraperitoneally or locally. Parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, intraperitoneal injection, intracranial and intrathecal administration for CNS tumors, and direct application to the target area, for example by a catheter or other placement device.

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The pharmaceutical compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Suitable pharmaceutically acceptable carriers may contain inert ingredients which do not unduly inhibit the biological activity of the compounds. The pharmaceutically acceptable carriers should be biocompatible, e.g., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

A pharmaceutically acceptable carrier for a pharmaceutical composition can also include delivery systems known to the art for entraining or encapsulating drugs, such as anti-cancer drugs. In some embodiments, the disclosed compounds can be employed with such delivery systems including, for example, liposomes, nanoparticles, nanospheres, nanodiscs, dendrimers, and the like. See, for example Farokhzad, O. C., Jon, S., Khademhosseini, A., Tran, T. N., Lavan, D. A., and Langer, R. (2004). "Nanoparticle-aptamer bioconjugates: a new approach for targeting prostate cancer cells." Cancer Res., 64, 7668-72; Dass, C. R. (2002). "Vehicles for oligonucleotide delivery to tumours." J. Pharm. Pharmacol., 54, 3-27; Lysik, M. A., and Wu-Pong, S. (2003). "Innovations in oligonucleotide drug delivery." J. Pharm. Sci., 92, 1559-73; Shoji, Y., and Nakashima, H. (2004). "Current status of delivery systems to improve target efficacy of oligonucleotides." Curr. Pharm. Des., 10, 785-96; Allen, T. M., and Cullis, P. R. (2004). "Drug delivery systems: entering the mainstream." Science, 303, 1818-22. The entire teachings of each reference cited in this paragraph are incorporated herein by reference.

Suitable doses can vary widely depending on the therapeutic being used. A typical pharmaceutical composition for intravenous administration would be about 0.1 mg to about 10 g per subject per day. However, in other embodiments, doses from about 1 mg to about 1 g, or from about 10 mg to about 1 g can be used. Single or multiple administrations of the compositions may be administered depending on the dosage and frequency as required and tolerated by the subject. In any event, the administration regime should provide a sufficient quantity of the composition of this invention to effectively treat the subject.

Useful dosages of the additional anticancer agents, such as antimitotic agents, and anti-cancer plant virus particles can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the additional anticancer agents and/or anti-cancer plant virus particles vary depending upon many different factors, including means of administration, target site, physiological state of the patient, whether the patient is human or an animal, other medications administered, and whether treatment is prophylactic or therapeutic.

The formulations may be conveniently presented in unit dosage form and may be prepared by any of the methods well known in the art of pharmacy. Preferably, such methods include the step of bringing the RNAi construct loaded icosahedral-shaped plant virus nanoparticles into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect.

One skilled in the art can readily determine an effective amount of RNAi construct loaded icosahedral-shaped plant virus nanoparticles and/or additional cancer therapeutics to be administered to a given subject, by taking into account factors such as the size and weight of the subject; the extent of disease penetration; the age, health and sex of the subject; the route of administration; and whether the administration is local or systemic. Those skilled in the art may derive appropriate dosages and schedules of administration to suit the specific circumstances and needs of the subject. For example, suitable doses of the RNAi construct loaded icosahedral-shaped plant virus nanoparticles to be administered can be estimated from the volume of cancer cells to be killed or volume of tumor to which the virus particles are being administered.

Useful dosages of the active agents can be determined by comparing their in vitro activity and the in vivo activity in animal models. Methods for extrapolation of effective dosages in mice, and other animals, to humans are known in the art. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the virus particles vary depending upon many different factors, including means of administration, target site, physiological state of the patient, whether the patient is human or an animal, characteristics of the subject, such as general health, age, sex, body weight and tolerance to drugs as well as the degree, severity and type of cancer, other medications administered, and whether treatment is prophylactic or therapeutic. The skilled artisan will be able to determine appropriate dosages depending on these and other factors using standard clinical techniques.

The methods described herein contemplate single as well as multiple administrations, given either simultaneously or over an extended period of time. A pharmaceutically acceptable composition containing the RNAi construct loaded icosahedral-shaped plant virus nanoparticles and/or additional cancer therapeutic can be administered at regular intervals, depending on the nature and extent of the cancer's effects, and on an ongoing basis. Administration at a "regular interval," as used herein, indicates that the therapeutically effective amount is administered periodically (as distinguished from a one-time dose). In one embodiment, the pharmaceutically acceptable composition containing the anti-cancer plant virus particles and/or an additional cancer therapeutic is administered periodically, e.g., at a regular interval (e.g., bimonthly, monthly, biweekly, weekly, twice weekly, daily, twice a day or three times or more often a day).

The administration interval for a single individual can be fixed, or can be varied over time, depending on the needs of the individual. For example, in times of physical illness or stress, or if disease symptoms worsen, the interval between doses can be decreased.

For example, the administration of RNAi construct loaded icosahedral-shaped plant virus nanoparticles and/or the additional therapeutic agent can take place at least once on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least once on week 1, 2, 3, 4, 5, 6, 7, 8, 9, 10, 11, 12, 13, 14, 15, 16, 17, 18, 19 or 20, or any combination thereof, using single or divided doses of every 60, 48, 36, 24, 12, 8, 6, 4, or 2 hours, or any combination thereof. Administration can take place at any time of day, for example, in the morning, the afternoon or evening. For instance, the administration can take place in the morning, e.g., between 6:00 a.m. and 12:00 noon; in the afternoon, e.g., after noon and before 6:00 p.m.; or in the evening, e.g., between 6:01 p.m. and midnight.

In some embodiments, the frequency of administration of RNAi construct loaded icosahedral-shaped plant virus nanoparticles can pose challenging for clinical implementation. Therefore, in some embodiments, the anti-cancer virus particles administered to a subject can be formulated in a slow release formulation in order to sustain immune stimulation by maintaining a therapeutic concentration of the RNAi construct loaded icosahedral-shaped plant virus nanoparticles, (e.g., at the site of a tumor) while alleviating the need for frequent administrations. In some embodiments, a slow release formulation can include a polymer-based hydrogel or a dendrimer.

In some embodiments, a slow-release formulation can include an RNAi construct loaded icosahedral-shaped plant virus nanoparticles dendrimer hybrid aggregate. The dendrimer can include a positively-charged polyamidoamine (PAMAM) dendrimer, such as a medium-sized generation 3 (G3) or generation 4 (G4) PAMAM dendrimer. Depending on the specific application, the plant virus-like particle-dendrimer hybrid aggregates can vary in size and release rate of the plant virus-like particle from the dendrimer when administered to a subject. In some embodiments, the anti-cancer virus particle-dendrimer hybrid aggregates are formulated so that at low salt the assembly of the aggregates is triggered and while under physiologic salt concentrations disassembly and anti-cancer virus particle release is induced.

Examples have been included to more clearly describe particular embodiments of the invention. However, there are a wide variety of other embodiments within the scope of the present invention, which should not be limited to the particular examples provided herein.

Example

In this Example, we describe a plant viral siRNA delivery platform. We established the application of CCMV to deliver siRNAs targeting first GFP for proof of concept and the forkhead box transcription factor (FOXA1) as a therapeutic target. To mediate cell trafficking and overcome the need for use of Lipofectamine, which has been co-delivered with plant viral capsids to promote the release of RNA cargo into the cytoplasm of mammalian cells facilitating protein expression, we appended CCMV with cell penetrating peptides (CPPs), specifically M-lycotoxin peptide L17E.

Materials and Methods

Purification and Propagation of Cowpea Chlorotic Mottle Virus (CCMV)

CCMV was propagated by mechanical inoculation using 5-10 μg of CCMV per leaf of cowpea plants, California Blackeye No. 5 (*Vigna unguiculata*). To isolate virus, infected leaf material was harvested 8 weeks post infection and blended with 2 mL of Buffer A (0.2 M sodium acetate buffer pH 4.8, 1 mM EDTA) per gram of tissue. The homogenate was squeezed through 3 layers of cheesecloth, collecting the liquid material. 1 volume of cold chloroform was added, mixed for 10 min and centrifuged at 15,000×g for 15 min. The supernatant was collected and precipitated by adding NaCl to a final concentration of 0.02 M and 8% PEG8000. The mixture was stirred overnight at 4° C., followed by centrifugation at 15,000×g for 10 minutes. The supernatant was discarded and the pellet was resuspended in 20 ml Buffer B (0.1 M sodium acetate buffer pH 4.8, 1 mM EDTA) by stirring for 1 h at 4° C., then centrifuged at 8000×g for 10 minutes. The supernatant was collected and centrifuged over a 20% sucrose cushion at 148,000×g for 2 hours. The pellet containing purified virus was then resuspended in 1 ml Buffer B. The concentration of the CCMV was determined at A260 and $\varepsilon=5.87$ $\mu L$ $\mu g^{-1}$ $cm^{-1}$.

Disassembly CCMV Particles to Obtain Coat Proteins

To disassemble CCMV to get coat proteins, virions were dialyzed using a 3.5K MWCO Slide-a-Lyzer dialysis cassette (Thermo Scientific) in disassembly buffer (0.5 M $CaCl_2$, 50 mM Tris-HCl, pH 7.5, 1 mM EDTA, 1 mM DTT, 0.5 mM PMSF) at 4° C. for 24 hours. Following dialysis, the solution was centrifuged at 12,000×g for 30 minutes at 4° C. to pellet the viral RNA. The supernatant was then centrifuged at 220,000×g for 2 hours at 4° C. to pellet any non-disassociated virus particles. The supernatant containing coat proteins was then dialyzed using a 3.5K MWCO Slide-a-Lyzer dialysis cassette in protein buffer (1 M NaCl, 20 mM Tris pH 7.2, 1 mM EDTA, 1 mM DTT, 1 mM PMSF) for 24 hours and stored at 4° C. The concentration of the CCMV coat proteins was determined at A280 and $\varepsilon=1.27$ $\mu l$ $\mu g^{-1}$ $cm^{-1}$.

Recombinant Production and Purification of CCMV Coat Proteins in *E. coli*

The CCMV coat protein (573 bp) was cloned into the vector pET28a(+) (Novagen) via NdeI and BamHI. The pET281/CCMV-CP construct was transformed into the *E. coli* strain ClearColi BL21(DE3) (Lucigen). 2 mL of an overnight culture was transferred to 400 mL of LB-Miller broth with 50 mg $L^{-1}$ kanamycin and grown at 37° C. until OD600 reached 0.6-0.8. Protein expression was induced using 0.5 mM IPTG and the culture was allowed to grow at 22° C. for 16 hours. The cultures were then placed on ice for 10 minutes and cells were harvested by centrifugation at 15,000×g for 20 min at 4° C. The supernatant was discarded and the pellet was resuspended in 20 mL bacteria lysis buffer (GoldBio) and incubated on ice for 5 minutes. Lysozyme was then added at a final concentration of 1 mg $mL^{-1}$ and the cell suspension was incubated at 37° C. for 1 hour. PMSF was then added at a final concentration at 1 mM and the solution was sonicated on a Q500 Sonicator (QSonic) for 15 minutes using 5 second pulses at an intensity of 40%. The solution was centrifuged at 15,000×g for 30 min at 4° C. and the supernatant was passed through a 0.45 m filter. The cell suspension was loaded through a HisPur Cobalt Chromatography Cartridge (Thermo Scientific) and His-tagged CCMV coat proteins were collected through affinity purification as per manufacturer's protocol. 1.5 mL elutions were collected from the column using elution buffer (50 mM sodium phosphate, 300 mM sodium chloride, 250 mM imidazole; pH 7.4). Elution fractions were measured using UV-visible spectroscopy to verify that proteins were present in the fractions, and fractions were pooled accordingly. Pooled fractions of CCMV coat proteins were then dialyzed in protein buffer (1 M NaCl, 20 mM Tris pH 7.2, 1 mM EDTA, 1 mM DTT, 1 mM PMSF) for 24 hours at 4° C. using a 3.5K MWCO Slide-a-Lyzer dialysis cassette (Thermo Scientific). Dialyzed coat proteins were stored at 4° C.

Reassembly of CCMV

For reassembly, coat proteins subunits and the desired dicer substrate siRNA (IDT) were mixed in a 6:1 (w/w) ratio in protein buffer. The mixture was dialyzed in a 7K MWCO Slide-a-Lyzer dialysis cassette (Thermo Scientific) against RNA assembly buffer (50 mM Tris pH 7.2, 50 mM NaCl, 10 mM KCl, 5 mM $MgCl_2$, 1 mM DTT) for at least 6 hours at 4° C., then immediately dialyzed against virus suspension buffer (50 mM sodium acetate buffer pH 4.5, 8 mM magnesium acetate) for at least 6 hours at 4° C. The assembly was purified by centrifugation through a 100 k Amicon Ultra-0.5 mL centrifugal filter (EMD Millipore) at 3000×g for 5 minutes, followed by 3 washes with virus suspension buffer.

Transmission Electron Microscopy

CCMV samples were diluted to 0.5-0.8 mg ml-1 in water and 20 μL was applied to glow-discharged carbon-coated 200 mesh grids (Electron Microscopy Sciences) for 2 minutes. Excess sample was blotted from the grids with Whatman Grade 1 filter paper, and the grids were rinsed twice with distilled water before staining with 2% (w/v) uranyl acetate for 2 minutes. Grids were imaged on a FEI Tecnai Spirit T12 transmission electron microscope operated at 200 kV.

Chemical Labelling of CCMV

Sulfo-Cy5 NHS ester (Lumiprobe) was conjugated to CCMV through NHS chemistry to the exterior surface lysines. The reaction was performed using a 100 molar excess of dye with CCMV in 0.1 M HEPES pH 7.0, 5 mM $MgCl_2$ buffer containing 10% (v/v) DMSO. The reaction was allowed to proceed overnight at room temperature with gentle agitation. The reaction was purified with ultracentrifugation at 150,000×g for 1 hour over a 30% (w/v) sucrose cushion.

The peptide m-lycotoxin was conjugated to CCMV via an $SM(PEG)_4$ crosslinker (Thermo Scientific) through NHS chemistry to the exterior surface lysines. The reaction was performed using a 600 molar excess of $SM(PEG)_4$ with CCMV in 0.1 M HEPES pH 7.0, 5 mM $MgCl_2$ buffer for 2 hours at room temperature with gentle agitation. Excess $SM(PEG)_4$ was removed via centrifugation through a PD MidiTrap G-25 Sample Preparation Column (GE Healthcare). M-lycotoxin was reacted to CCMV-$SM(PEG)_4$ at 600 molar excess with gentle agitation over night at room temperature. The reaction was purified with ultracentrifugation at 150,000×g for 1 hour over a 30% (w/v) sucrose cushion.

Gel Electrophoresis

For denaturing gel electrophoresis, samples were denatured by heating at 100° C. for 10 minutes in NuPage 4×LDS Sample loading buffer (Thermo Scientific). CCMV (10 μg) were loaded on 12% NuPage Bis-Tris protein gels (Thermo Scientific) and run in 1×MOPs buffer at 200V for 35 minutes. Gels were stained with Coomassie Blue. For native gel electrophoresis, 10 μg of sample was loaded into 0.8% (w/v) TAE agarose gels with 1× GelRed (Biotium) in 1× TAE buffer and run at 90V for 40 minutes. All gels were imaged on an AlphaImager HP (Protein Simple) and analyzed with Fiji.

Cell Culture

HeLa and MCF-7 cells were obtained from the ATCC (Manassas, VA). HeLa/GFP cells were obtained from Cell Biolabs, Inc (San Diego, CA). Cells were grown and maintained in Dulbecco's Modified Eagle's medium (DMEM, Cellgro) supplemented with 10% (v/v) fetal bovine serum (Atlanta Biologicals) and 1% (v/v) penicillin/streptomycin (Gibco). Cells were grown at 37° C. in a 5% $CO_2$ humidified incubator.

Flow Cytometry

HeLa cells were collected using enzyme-free Hank's cell dissociation buffer (Gibco) and resuspended to $2.5\times10^6$ cells $mL^{-1}$. Cells ($5\times10^5$ cells in 0.2 mL) were added to 96-well V-bottom plates (Corning 3897). CCMV particles ($1\times10^5$ particles per cell) were added in triplicate and incubated for 6 hours at 37° C. in a 5% $CO_2$ humidified incubator. Following incubation, half of the cells were centrifuged at 500×g and resuspended in DPBS with 1 mg $mL^{-1}$ pronase (Sigma-Aldrich) and treated at room temperature for 15 minutes. All cells were then centrifuged at 500×g and washed with FACS buffer (1 mM EDTA, 1% (v/v) FBS, 25 mM HEPES pH 7.0 in PBS) twice and fixed in 2% (v/v) paraformaldehyde in FACS buffer for 10 minutes. After fixing, cells were further washed in FACS buffer twice. Following washing, cells were resuspended in PBS and analyzed on a BD LSRII instrument. At least 10,000 gated events were recorded and data were analyzed using FlowJo 10.2 software.

Confocal Microscopy

HeLa or HeLa/GFP cells were seeded on circular coverslips in a 24 well suspension plate (25,000 cells in 0.5 mL). Cells were allowed to grow for 24 hours at 37° C. in a 5% $CO_2$ humidified incubator before $1\times10^7$ particles per cell were added. Following incubation with particles for 24 hours, cells were washed three times with DPBS, then fixed in 5% (v/v) paraformaldehyde, 0.3% (v/v) glutaraldehyde in DPBS for 10 minutes. Cells were then washed three times with DPBS. Cellular components were stained as follows: (A) for HeLa cells: (i) cell membranes were stained with wheat germ agglutinin, Alexa Fluor 555 conjugate (WGA-555; Invitrogen), 1:1000 in 5% (v/v) goat serum in DPBS; (ii) lysosomes were stained with an Alexa Fluor 488 anti-human LAMP-1 antibody (BioLegend), 1:500 in 5% (v/v) goat serum in DPBS); (iii) nuclei were stained with DAPI found in the mounting medium. (B) For HeLa/GFP cells: (i) cell membranes were stained with wheat germ agglutinin, Alexa Fluor 555 conjugate (WGA-555; Invitrogen), 1:1000 in 5% (v/v) goat serum in DPBS; (ii) nuclei were stained with DAPI found in the mounting medium; (iii) CCMV particles were stained with rabbit anti-CCMV antibody, 1:200 in 5% (v/v) goat serum in DPBS for 1 hour followed by goat anti-rabbit secondary antibody tagged with Alexa Fluor 647, 1:500 in 5% (v/v) goat serum in DPBS. Cells were first stained with WGA-555, then permeabilized with 0.2% (v/v) Triton X-100 for 2 minutes and then blocked with 10% (v/v) goat serum in DPBS for 1 hour. Cells were washed three times with DPBS in between treatments. Following all staining, coverslips were mounted onto slides with Fluoroshied with DAPI (Sigma-Aldrich) histology mounting medium and sealed with clear nail polish. Confocal images were obtained on a Leica TCS SPE confocal microscope with a 63× oil immersion objective. Images were analyzed with Fiji.

Cell Treatment with siRNA and Quantitative Real-Time PCR

HeLa/GFP or MCF-7 cells were plated in a 24-well treated plate at 62,500 cells $mL^{-1}$. 10,000,000 particles per cell of CCMV/CCM-siRNA was added to cells and incubated for 24 hours at 37° C. in a 5% $CO_2$ humidified incubator. Treatments were performed in triplicate. For RNA extraction, cell media was removed and 0.5 mL of TRI- Reagent (Sigma-Aldrich) was added to the cells. Cell lysate was passed several times through a pipette to form a homogenous lysate. RNA was extracted using TRI-Reagent as per manufacturer's protocol. 1 μg of RNA was used to make cDNA using the iScript gDNA Clear cDNA synthesis kit (Bio-Rad). cDNA was diluted 1:10 and 2 μL was used in a 20 μL qPCR reaction containing 1× SsoAdvanced Universal SYBR Green Supermix (Bio-Rad) and 250 nM each of forward and reverse primer (IDT). qPCR was performed using a CFX-96 touch machine (Bio-Rad) with the following parameters: 95° C. for 30 seconds, then 40 cycles of 98° C. for 10 seconds, 15 seconds at 60° C., followed by a melting curve. Data was analyzed with CFX Maestro software (Bio-Rad).

Statistical Analysis

Results are presented as means±the standard deviation (SD). Statistical comparisons between groups were performed using a one-way ANOVA followed by the appropriate post hoc tests. Significance was accepted at p values<0.05.

| dicer substrate siRNA sequence | | |
|---|---|---|
| eGFP siRNA | sense | 5' AACGAGAAGCGCGAUCACAUGG UCC 3' (SEQ ID NO: 9) |
| | anti-sense | 5' GGACCAUGUGAUCGCGCUUCUC GUUGG 3' (SEQ ID NO: 10) |
| FOXA1 siRNA | sense | 5' GAGAGAAAAAUCAACAGCAAA CAA 3' (SEQ ID NO: 11) |
| | anti-sense | 5' UUGUUUGCUGUUGAUUUUUCU CUCUU 3' (SEQ ID NO: 12) |
| Primer | | |
| eGFP | forward | 5' GAACCGCATCGAGCTGAA 3' (SEQ ID NO: 13) |
| | reverse | 5' TGCTTGTCGGCCATGATATAG 3' (SEQ ID NO: 14) |
| FOXA1 | forward | 5' GGGGGTTTGTCTGGCATAGC 3' (SEQ ID NO: 15) |
| | reverse | 5' GCACTGGGGGAAAGGTTGTG 3' (SEQ ID NO: 16) |
| ACTB | forward | 5' AGGGTGAGGATGCCTCTCTT 3' (SEQ ID NO: 17) |
| | reverse | 5' GGCATGGGTCAGAAGGATT 3' (SEQ ID NO: 18) |

Dicer Substrate siRNA
eGFP siRNA

Sense
(SEQ ID NO: 19)
5' AACGAGAAGCGCGAUCACAUGGUCC 3'

Antisense
(SEQ ID NO: 20)
5' GGACCAUGUGAUCGCGCUUCUCGUUGG 3'

FOXA1 siRNA

Sense
(SEQ ID NO: 21)
5' GAGAGAAAAAUCAACAGCAAACAA 3'

Antisense
(SEQ ID NO: 22)
5' UUGUUUGCUGUUGAUUUUUCUCUCUU 3'

NEGATIVE CONTROL siRNA
IDT Negative Control DsiRNA NS1
Cy3-LABELED siRNA
eGFP-Cy3 siRNA (GE Dharmacon)
Primers:

eGFP-F
(SEQ ID NO: 23)
5' GAACCGCATCGAGCTGAA 3' eGFP-R
(SEQ ID NO: 24)
5' TGCTTGTCGGCCATGATATAG 3'

FOXA1-F
(SEQ ID NO: 25)
5' GGGGGTTTGTCTGGCATAGC 3'

FOXA1-R
(SEQ ID NO: 26)
5' GCACTGGGGGAAAGGTTGTG 3'

ACTB-F
(SEQ ID NO: 27)
5' AGGGTGAGGATGCCTCTCTT 3'

ACTB-R
(SEQ ID NO: 28)
5' GGCATGGGTCAGAAGGATT 3'

CCMV CP Sequence:

(SEQ ID NO: 29)
ATGTCTACAGTCGGAACAGGGAAGTTAACTCGTGCACAACGAAGGGCTGC

GGCCCGTAAGAACAAGCGGAACACTCGTGTGGTCCAACCTGTTATTGTAG

AACCCATCGCTTCAGGCCAAGGCAAGGCTATTAAAGCATGGACCGGTTAC

AGCGTATCGAAGTGGACCGCCTCTTGTGCGGCTGCCGAAGCTAAAGTAAC

CTCGGCTATAACTATCTCTCTCCCTAATGAGCTATCGTCCGAAAGGAACA

AGCAGCTCAAGGTAGGTAGAGTTTTATTATGGCTTGGGTTGCTTCCCAGT

GTTAGTGGCACAGTGAAATCCTGTGTTACAGAGACGCAGACTACTGCTGC

TGCCTCCTTTCAGGTGGCATTAGCTGTGGCCGACAACTCGAAAGATGTTG

TCGCTGCTATGTACCCCGAGGCGTTTAAGGGTATAACCCTTGAACAACTC

GCCGCGGATTTAACGATCTACTTGTACAGCAGTGCGGCTCTCACTGAGGG

CGACGTCATCGTGCATTTGGAGGTTGAGCATGTCAGACCTACGTTTGACG

ACTCTTTCACTCCGGTGTATTAG

Results

CCMV particles were produced in black-eyes peas No. 5 by mechanical inoculation and purification from homogenized leaves by chloroform extraction, PEG precipitation, and ultracentrifugation; as an alternative, we also produced CCMV coat proteins using an E. coli expression system. First, we established whether CCMV would enter mammalian cells using HeLa cells, a well-established cancer cell line. For imaging and flow cytometry analysis, Cyanine5 (Cy5)-labeled CCMV was obtained using an NHS-activated Cy5 enabling coupling to CCMV's surface lysines (Supplementary Information). UV/vis spectroscopy indicated that CCMV was labeled with approximately 60 Cy5 dyes per CCMV particle.

Figure 1B:
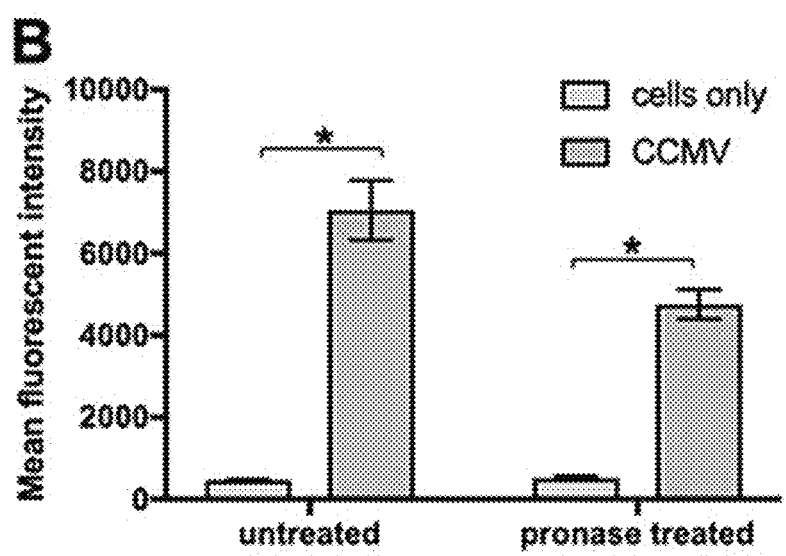
Figure 1C:
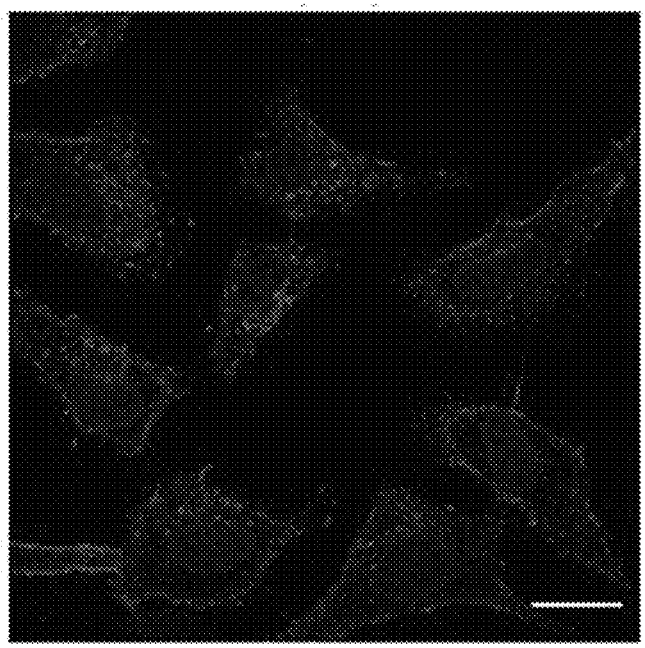
Figure 1D:
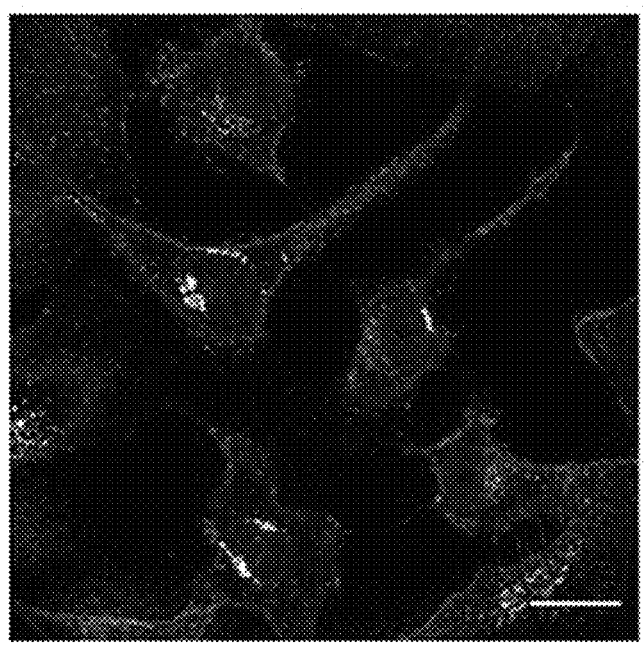
Figure 2A:
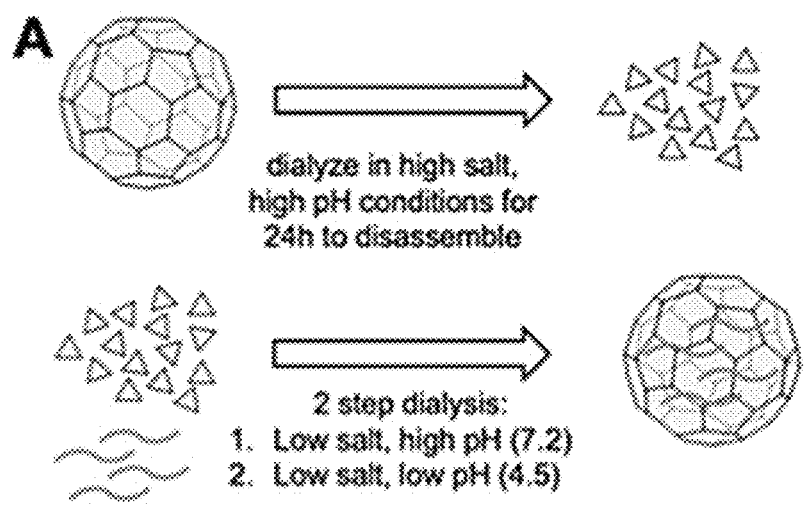
FIGS. 2(A-F) are illustrations and images showing the characterization of reassembled CCMV particles. (A) Scheme for disassembly of whole CCMV virions to coat proteins, then the reassembly around heterologous siRNAs to make CCMV-siRNA. (B) Transmission electron micrograph of CCMV particles. (C) Transmission electron micrograph of reassembled CCMV particles. Scale bar=50 nm. (D) SDS-PAGE analysis of CCMV after conjugation with various molar excesses (600, 900, 1200:1 L17E:CCMV) of the cell penetrating peptide m-lycotoxin, L17E (CPP). The CCMV single coat protein is approximately 20 kDa. Successful conjugation is indicated by the higher molecular weight band (see arrow). (E) SDS-PAGE analysis of reassembled CCMV encapsulated eGFP siRNA or negative control siRNA. Lanes 1, 4=CCMV; 2, 5=reassembled CCMV; 3, 6=reassembled L17E-labeled CCMV. (F) Agarose gel electrophoresis showing successful encapsulation of siRNA in reassembled CCMV. Lane 1-CCMV (positive control); 2=CCMV-eGFPsiRNA; 3=CCMV-neg-siRNA.
Figure 2B:
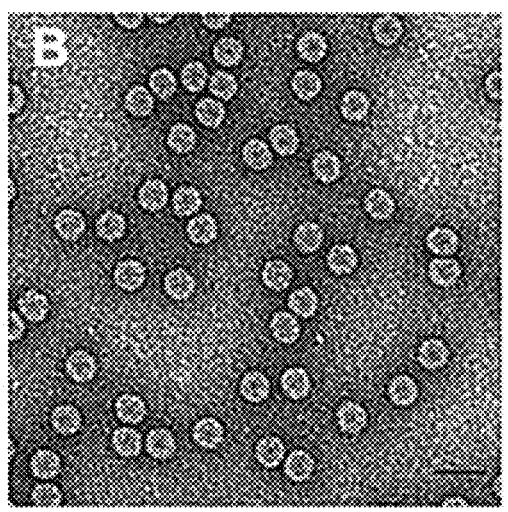
Figure 2C:
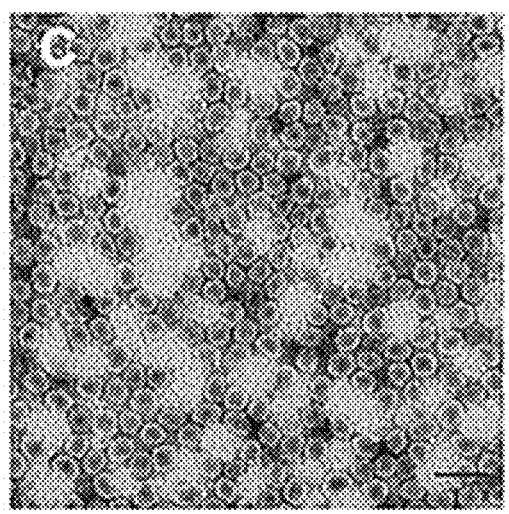

For quantitative flow cytometry assays, $1 \times 10^5$ CCMV per cell were added and particles were allowed to interact with HeLa cells for 6 hours. Cells were treated with pronase to assess the level of surface-bound CCMV. Similarly, confocal microscopy studies were performed; flow cytometry and imaging data are in agreement and indicate that CCMV indeed enters HeLa cells; only a fraction of particles remain surface bound and hence are removed by the pronase treatment (FIGS. 1A-B). Significant co-localization with cell surface marker wheat germ agglutinin was not observed; however, staining with an endolyosomal marker (Lamp-1) revealed that CCMV is partially entrapped within endolysosomal vesicles (Manders coefficient of MCCMV vs. LAMP-1=0.32, FIGS. 1C-D); i.e. data suggest that CCMV at least partially escapes the endolyosomal compartment. Based on these encouraging data, we prepared siRNA-laden CCMV with and without CPP L17E.

siRNA encapsulation was achieved making use of pH- and salt-controlled, dis- and assembly methods; to yield CCMV loaded with siRNA, the dicer substrate siRNA as well as their non-targeted control RNAs were added at a 6:1 (w/w) ratio (FIG. 2A). Transmission electron microscopy (TEM) imaging revealed that reconstituted CCMV carrying siRNAs were structurally sound forming 30 nm-sized icosahedral particles (FIGS. 2B,C).

Next, a CPP was added; specifically, we chose the M-lycotoxin peptide L17E. This peptide was initially derived from spider venom; the L17E has Glu additions to reduce the overall positive charge and therefore enhance function. Data suggest that the L17E preferentially disrupts endolysosomal over plasma membranes; furthermore, when added to biologics (such as antibodies), L17E promotes cell uptake by micropinocytosis, thus making it a promising candidate for nanoparticle-mediated gene delivery. We reasoned that the addition of the CPP would be beneficial and increase efficacy of siRNA delivery, because our data showed that CCMV, at least in part, is entrapped in the endolysosomal compartment (see FIG. 1).

Figure 2D:
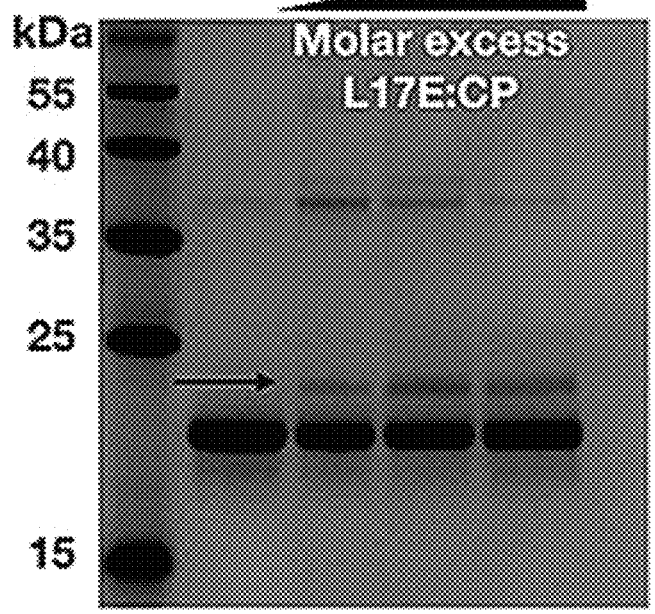
Figure 2E:
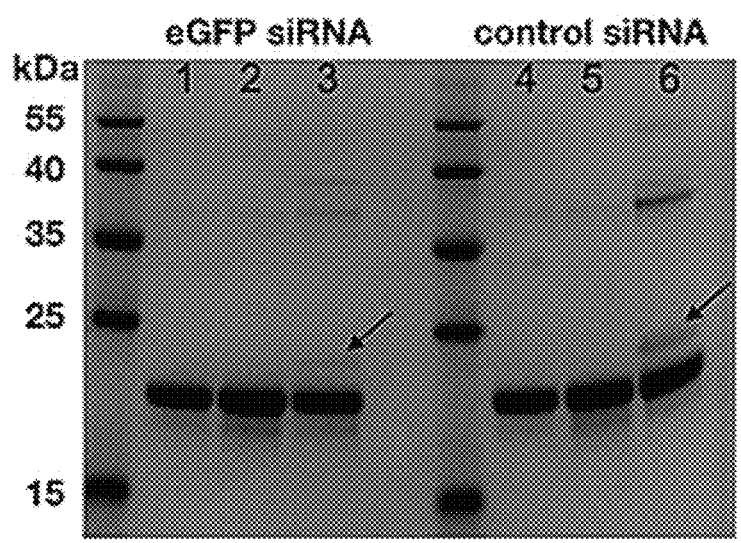
Figure 2F:
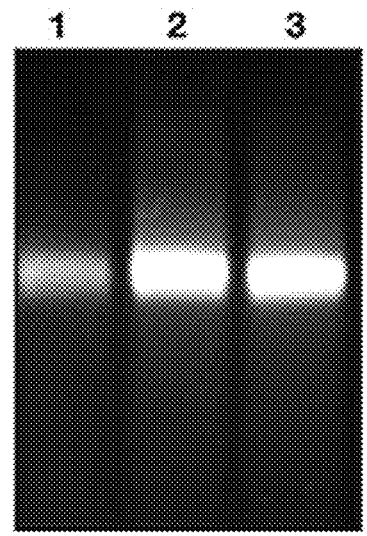

The following peptide was synthesized: IWL-TALKFLGKHAAKHEAKQQLSKL (SEQ ID NO: 8) with C-terminal amide or Gly-Gly-Cys linker; the latter was used for bioconjugation to CCMV's surface lysines using an SM(PEG)4 linker (detailed protocols are listed in the Supplementary Information). Varying the peptide:CCMV ratio did not have significant impact on the labeling efficiency, SDS-PAGE revealed that ~15-20% of CCMV's coat proteins were modified using molar ratios of 600, 900, and 1200:1 peptide:CCMV (FIG. 2D); or in other words, the conjugation yielded CCMV displaying ~30 L17E peptides per particle (FIG. 2D). Quantification was carried out by measuring the band density comparing L17E-labeled CP vs. native CP using band analysis tool and ImageJ software. Using these methods, we then produced dual-functional CCMV loaded with siRNA and tagged with L17E peptides (FIG. 2E); SDS-PAGE revealed successful conjugation of the CPP, and agarose gel electrophoresis using a nucleic acid stain revealed successful encapsulation of the siRNA cargo (FIG. 2F). Using a fluorescently-labeled eGFP-Cy3 siRNA we determined that CCMV could encapsulated 2-3 µM siRNAs.

Figure 3G:
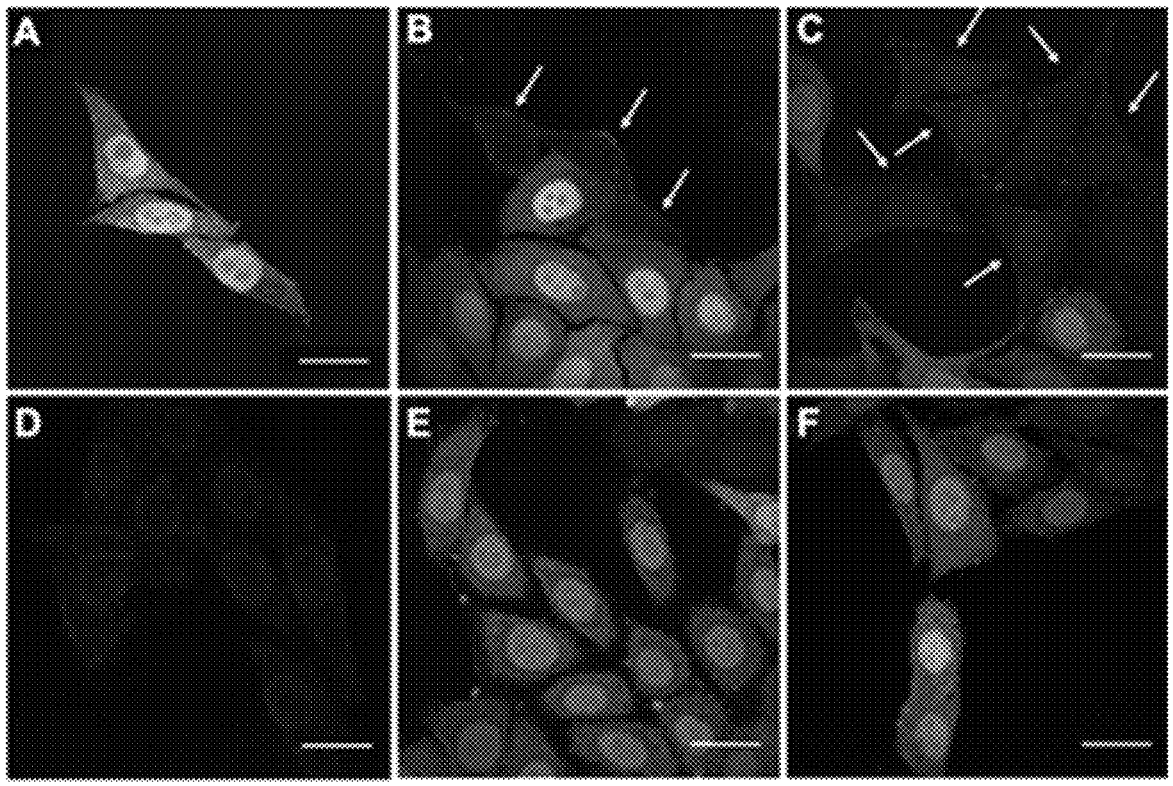
FIGS. 3(A-G) are microscopic images and a graph showing siRNA silencing of HeLa/GFP cells. (A-F) Confocal microscopy of HeLA/GFP cells treated with different particle formulations for 24 hours. Loss of eGFP expression occurred when cells were treated with siRNA targeting eGFP. (A) HeLa/GFP cells only control. (B-C) Cells treated with CCMV-eGFPsiRNA and CCMV-mlyco-eGFPsiRNA (mlyco=L17E peptide), respectively. CCMV particles are present in cells with no eGFP expression. (D) Cells treated with lipofectamine+eGFPsiRNA; (E-F) with CCMV-neg-siRNA and CCMV-mlyco-negsiRNA. Particles are visible in the cell indicating cell uptake, but no silencing of eGFP present. Scale bar=25 μm. (G) Quantitative real-time PCR showing relative levels of eGFP expression in cells after various treatments. Statistically significant changes in eGFP expression relative to the cells only control after a one-way ANOVA are indicated with *.
Figure 3G:
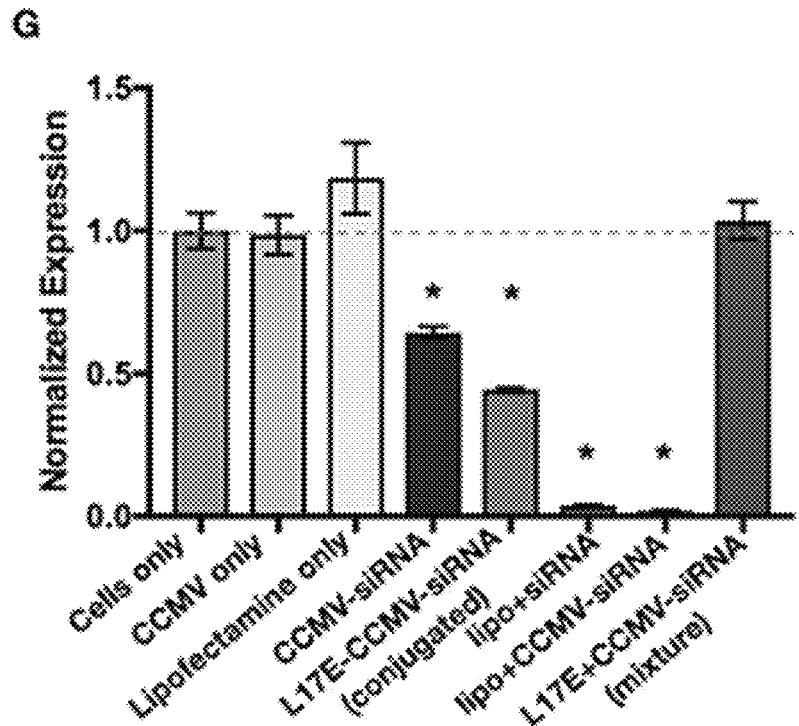

First, for proof-of-concept, we used GFP-expressing HeLa cells and treated these with siRNA-loaded CCMV particles with and without L17E peptide; control experiments included the use of free siRNA and CCMV-delivered siRNA in combination with lipofectamine; we used target and non-target siRNAs (at a 7.5-10 nM concentration). Confocal microscopy revealed successful gene silencing mediated by the plant viral siRNA delivery vector (FIGS. 3A-F): comparing siRNA-loaded CCMV vs. CCMV-L17E it was apparent that the addition of the L17E peptide increased efficacy; GFP expression was silenced across more cells. For either nanoparticle formulation it was apparent that GFP silencing was not achieved uniformly across all cells; however, cells that showed positive signals for CCMV (shown in in FIG. 3), loss of GFP fluorescence was apparent (FIGS. 3B-C). Quantitative analysis using real time qPCR showed that indeed addition of the L17E CPP increased the effectiveness of the gene silencing approach; while CCMV alone yielded 30% downregulation of GFP expression, the siRNA-loaded L17E-CCMV formulation achieved 50% downregulation of GFP mRNA. Interestingly, mixing CCMV with the L17E peptide did not give rise to gene silencing (sample: L17E+CCMV-siRNA). A previous study showed that physical mixtures of the L17E peptide and antibodies enabled cytosolic delivery of therapeutic antibodies. In contrast, L17E+CCMV mixtures resulted in aggregation, likely based on the polyvalent nature of the CCMV particles with its overall negative surface charge building multi-particle interlinkages with the positively-charged L17E peptide (pI~10); therefore, preventing cell uptake, cargo delivery, and gene silencing (FIG. 3G).

Figure 4:
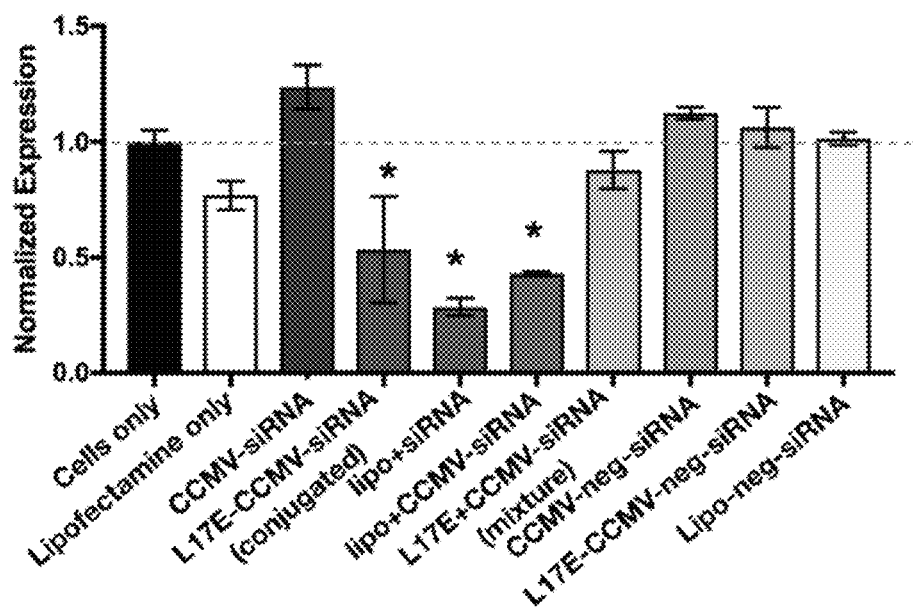
FIG. 4 is a graph showing quantitative real time PCR assessing the level of FOXA1 expression in MCF-7 cells after treatment with siRNAs, delivered with lipofectamine or encapsulated within CCMV and CCMV conjugated with m-lycotoxin L17E peptide (CPP). Statistically significant changes in FOXA1 expression relative to the cells only control after a one-way ANOVA are indicated with *.

Lastly, we selected siRNAs to target FOXA1 as a potential therapeutic target in breast cancer or prostate cancer. Data indicate a critical role of FOXA1 in cell proliferation and studies suggest that gene silencing is indeed a successful strategy to inhibit cell proliferation and induce G0/G1 arrest. Here we tested whether CCMV formulated with siRNAs targeting FOXA1 would allow gene silencing using the breast cancer cell line MCF-7. Data indicate that siRNA-loaded CCMV alone was not effective in silencing the target gene FOXA1; however, conjugation of the CPP L17E restored efficacy leading to knockdown of FOXA1 mRNA levels by 50%, matching the effectiveness of lipofectamine (FIG. 4). However, also here we found that the L17E peptide needed to be covalently conjugated and displayed on CCMV; physical mixtures of siRNA-loaded CCMV+L17E peptide had no efficacy, which again can be explained by instability of this mixture.

We demonstrate that siRNA molecules can be effectively loaded into CCMV nanoparticles, while target gene knockdown using the native CCMV protein was observed using HeLa cells overexpressing GFP, only CCMV with appended CPPs, here M-lycotoxin peptide L17E, were efficient in silencing FOXA1 gene. While plant viruses offer advantageous properties for biological applications, they have not evolved the sophisticated machinery of mammalian viral vectors, to navigate the cellular compartments of mammalian cells. Therefore, the addition of CPPs or other strategies that would prime endolyosomal escape likely will be beneficial for the development of effective plant viral gene delivery vectors. Similar observations have been made using the capsids from bacteriophages which, like plant viruses, offer a highly intriguing nanotechnology platform but lack mechanism to engage with mammalian cells. Nevertheless, gene silencing using the native CCMV capsid was apparent and imaging data indicate that the CCMV nanoparticle was only partially trapped within the endolysosomal compartment.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

What is claimed is:

1. A nanoparticle comprising a cowpea chlorotic mottle virus (CCMV); a siRNA; and an L17E M-lycotoxin peptide, wherein the siRNA is noncovalently loaded within the CCMV.

2. The nanoparticle of claim 1, the siRNA comprising a siRNA targeting the forkhead box transcription factor (FOXA1) oncogene.

3. The nanoparticle of claim 1, wherein the L17E M-lycotoxin peptide is linked to the exterior surface of the CCMV.

4. A method of treating hormone dependent breast cancer in a subject, comprising administering to the subject a therapeutically effective amount of a nanoparticle including a cowpea chlorotic mottle virus (CCMV), an siRNA targeting the forkhead box transcription factor (FOXA1) oncogene, and a L17E M-lycotoxin peptide, wherein the RNAi construct is encapsulated within the CCMV.

5. The method of claim 4, wherein the L17E M-lycotoxin peptide is linked to the exterior surface of the CCMV plant virus nanoparticle.

6. The method of claim 4, wherein the nanoparticle is administered to the subject systemically.

7. The method of claim 4, further comprising administering a therapeutically effective amount of an additional anticancer agent or therapy to the subject.

8. The method of claim 7, wherein the additional anticancer agent is selected from an antitumor agent and an anti-hormonal agent.

9. The method of claim 7, wherein the additional anticancer therapy is selected from radiation therapy, brachytherapy and an ablation therapy.

10. A method of treating hormone dependent breast cancer in a subject, comprising administering to the subject a therapeutically effective amount of nanoparticle comprising a cowpea chlorotic mottle virus (CCMV) virus particle, an siRNA targeting the forkhead box transcription factor (FOXA1) oncogene, wherein the siRNA is encapsulated within the CCMV virus particle, and one or more endolysosomal release agents comprising a L17E M-lycotoxin peptide.

11. The nanoparticle of claim 1, the siRNA comprising an oncogene targeted siRNA.

* * * * *

SEQUENCE LISTING

<160> NUMBER OF SEQ ID NOS: 29

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct

<400> SEQUENCE: 1

Gly Arg Lys Lys Arg Arg Gln Arg Arg Pro Gln
1               5                   10

<210> SEQ ID NO 2
<211> LENGTH: 21
<212> TYPE: PRT
<213> ORGANISM: Artificial Sequence
<220> FEATURE:
<223> OTHER INFORMATION: Synthetic Construct

<400> SEQUENCE: 2

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 3
<211> LENGTH: 16
<212> TYPE: PRT
<213> ORGANISM: Artificial Sequence
<220> FEATURE:
<223> OTHER INFORMATION: Synthetic Construct

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 25
<212> TYPE: PRT
<213> ORGANISM: Artificial Sequence
<220> FEATURE:
<223> OTHER INFORMATION: Synhetic Construct

<400> SEQUENCE: 4

Ile Trp Leu Thr Ala Leu Lys Phe Leu Gly Lys His Ala Ala Lys His
1               5                   10                  15

Glu Ala Lys Gln Gln Leu Ser Lys Leu
            20                  25

<210> SEQ ID NO 5
<211> LENGTH: 12
<212> TYPE: PRT
<213> ORGANISM: Artificial Sequence
<220> FEATURE:
<223> OTHER INFORMATION: Synthetic Construct

<400> SEQUENCE: 5

Ala Ala Val Leu Leu Pro Val Leu Leu Ala Ala Pro
1               5                   10

<210> SEQ ID NO 6
<211> LENGTH: 24
<212> TYPE: PRT
<213> ORGANISM: Artificial Sequence
<220> FEATURE:

<223> OTHER INFORMATION: Synthetic Construct

<400> SEQUENCE: 6

His Pro Ile Gln Ile Ala Ala Phe Leu Ala Arg Ile Pro Pro Ile Ser
1               5                   10                  15

Ser Ile Gly Thr Cys Ile Leu Lys
            20

<210> SEQ ID NO 7
<211> LENGTH: 19
<212> TYPE: RNA
<213> ORGANISM: Artificial Sequence
<220> FEATURE:
<223> OTHER INFORMATION: Synthetic Construct

<400> SEQUENCE: 7
ggacgaggac gagcacuuc                                            19

<210> SEQ ID NO 8
<211> LENGTH: 25
<212> TYPE: PRT
<213> ORGANISM: Artificial Sequence
<220> FEATURE:
<223> OTHER INFORMATION: Synthetic Construct

<400> SEQUENCE: 8

Ile Trp Leu Thr Ala Leu Lys Phe Leu Gly Lys His Ala Ala Lys His
1               5                   10                  15

Glu Ala Lys Gln Gln Leu Ser Lys Leu
            20                  25

<210> SEQ ID NO 9
<211> LENGTH: 25
<212> TYPE: RNA
<213> ORGANISM: Artificial Sequence
<220> FEATURE:
<223> OTHER INFORMATION: Synthetic Construct

<400> SEQUENCE: 9
aacgagaagc gcgaucacau ggucc                                     25

<210> SEQ ID NO 10
<211> LENGTH: 27
<212> TYPE: DNA
<213> ORGANISM: Artificial Sequence
<220> FEATURE:
<223> OTHER INFORMATION: Synthetic Construct

<400> SEQUENCE: 10
ggaccaugug aucgcgcuuc ucguugg                                   27

<210> SEQ ID NO 11
<211> LENGTH: 25
<212> TYPE: RNA
<213> ORGANISM: Artificial Sequence
<220> FEATURE:
<223> OTHER INFORMATION: Synthetic Construct

<400> SEQUENCE: 11
gagagaaaaa aucaacagca aacaa                                     25

<210> SEQ ID NO 12
<211> LENGTH: 27
<212> TYPE: RNA
<213> ORGANISM: Artificial Sequence

```
<220> FEATURE:
<223> OTHER INFORMATION: Synthetic Construct

<400> SEQUENCE: 12
uuguuugcug uugauuuuuu cucucuu                                              27

<210> SEQ ID NO 13
<211> LENGTH: 18
<212> TYPE: DNA
<213> ORGANISM: Artificial Sequence
<220> FEATURE:
<223> OTHER INFORMATION: Synthetic Construct

<400> SEQUENCE: 13
gaaccgcatc gagctgaa                                                        18

<210> SEQ ID NO 14
<211> LENGTH: 21
<212> TYPE: DNA
<213> ORGANISM: Artificial Sequence
<220> FEATURE:
<223> OTHER INFORMATION: Synthetic Contruct

<400> SEQUENCE: 14
tgcttgtcgg ccatgatata g                                                    21

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15 ggggggtttgt ctggcatagc                                                     20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
gcactggggg aaaggttgtg                                                      20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
agggtgagga tgcctctctt                                                      20

<210> SEQ ID NO 18
<211> LENGTH: 19
<212> TYPE: DNA
<213> ORGANISM: Artificial Sequence
<220> FEATURE:
<223> OTHER INFORMATION: Synthetic Construct

<400> SEQUENCE: 18
ggcatgggtc agaaggatt                                                       19
```

```
<210> SEQ ID NO 19
<211> LENGTH: 25
<212> TYPE: RNA
<213> ORGANISM: Artificial Sequence
<220> FEATURE:
<223> OTHER INFORMATION: Synthetic Construct

<400> SEQUENCE: 19
aacgagaagc gcgaucacau ggucc                                              25

<210> SEQ ID NO 20
<211> LENGTH: 27
<212> TYPE: RNA
<213> ORGANISM: Artificial Sequence
<220> FEATURE:
<223> OTHER INFORMATION: Synthetic Construct

<400> SEQUENCE: 20
ggaccaugug aucgcgcuuc ucguugg                                            27

<210> SEQ ID NO 21
<211> LENGTH: 25
<212> TYPE: RNA
<213> ORGANISM: Artificial Sequence
<220> FEATURE:
<223> OTHER INFORMATION: Synthetic Construct

<400> SEQUENCE: 21
gagagaaaaa aucaacagca aacaa                                              25

<210> SEQ ID NO 22
<211> LENGTH: 27
<212> TYPE: RNA
<213> ORGANISM: Artificial Sequence
<220> FEATURE:
<223> OTHER INFORMATION: Synthetic Construct

<400> SEQUENCE: 22
uuguuugcug uugauuuuuu cucucuu                                            27

<210> SEQ ID NO 23
<211> LENGTH: 18
<212> TYPE: DNA
<213> ORGANISM: Artificial Sequence
<220> FEATURE:
<223> OTHER INFORMATION: Synthetic Construct

<400> SEQUENCE: 23
gaaccgcatc gagctgaa                                                      18

<210> SEQ ID NO 24
<211> LENGTH: 21
<212> TYPE: DNA
<213> ORGANISM: Artificial Sequence
<220> FEATURE:
<223> OTHER INFORMATION: Synthetic Construct

<400> SEQUENCE: 24
tgcttgtcgg ccatgatata g                                                  21

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 25 ggggggtttgt ctggcatagc                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
gcactggggg aaaggttgtg                                                     20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
agggtgagga tgcctctctt                                                     20

<210> SEQ ID NO 28
<211> LENGTH: 19
<212> TYPE: DNA
<213> ORGANISM: Artificial Sequence
<220> FEATURE:
<223> OTHER INFORMATION: Synthetic Construct

<400> SEQUENCE: 28
ggcatgggtc agaaggatt                                                      19

<210> SEQ ID NO 29
<211> LENGTH: 573
<212> TYPE: DNA
<213> ORGANISM: Artificial Sequence
<220> FEATURE:
<223> OTHER INFORMATION: Synthetic Construct

<400> SEQUENCE: 29
atgtctacag tcggaacagg gaagttaact cgtgcacaac gaagggctgc ggcccgtaag        60
aacaagcgga acactcgtgt ggtccaacct gttattgtag aacccatcgc ttcaggccaa       120
ggcaaggcta ttaaagcatg gaccggttac agcgtatcga agtggaccgc ctcttgtgcg       180
gctgccgaag ctaaagtaac ctcggctata actatctctc tccctaatga gctatcgtcc       240
gaaaggaaca agcagctcaa ggtaggtaga gttttattat ggcttgggtt gcttcccagt       300
gttagtggca cagtgaaatc ctgtgttaca gagacgcaga ctactgctgc tgcctccttt       360
caggtggcat tagctgtggc cgacaactcg aaagatgttg tcgctgctat gtaccccgag       420
gcgtttaagg gtataaccct tgaacaactc gccgcggatt taacgatcta cttgtacagc       480
agtgcggctc tcactgaggg cgacgtcatc gtgcatttgg aggttgagca tgtcagacct       540
acgtttgacg actctttcac tccggtgtat tag                                    573